(12) United States Patent
Wang et al.

(10) Patent No.: US 8,236,822 B2
(45) Date of Patent: Aug. 7, 2012

(54) COMPOUNDS AS CANNABINOID RECEPTOR LIGANDS

(75) Inventors: Xueqing Wang, Evanston, IL (US); Michael J. Dart, Highland Park, IL (US); Bo Liu, Waukegan, IL (US)

(73) Assignee: Abbott Laboratories, Abbott Park, IL (US)

( * ) Notice: Subject to any disclaimer, the term of this patent is extended or adjusted under 35 U.S.C. 154(b) by 222 days.

(21) Appl. No.: 12/732,412

(22) Filed: Mar. 26, 2010

(65) Prior Publication Data

US 2010/0249086 A1   Sep. 30, 2010

Related U.S. Application Data

(60) Provisional application No. 61/163,953, filed on Mar. 27, 2009.

(51) Int. Cl.
| | | |
|---|---|---|
| A61K 31/4155 | (2006.01) | |
| A61K 31/415 | (2006.01) | |
| A61K 31/4178 | (2006.01) | |
| A61K 31/4168 | (2006.01) | |
| A61K 31/4196 | (2006.01) | |
| A61K 31/4245 | (2006.01) | |
| A61K 31/425 | (2006.01) | |
| A61K 31/426 | (2006.01) | |
| A61K 31/427 | (2006.01) | |
| A61K 31/433 | (2006.01) | |
| A61K 31/4427 | (2006.01) | |
| C07D 231/40 | (2006.01) | |
| C07D 249/14 | (2006.01) | |
| C07D 261/14 | (2006.01) | |
| C07D 263/48 | (2006.01) | |
| C07D 271/113 | (2006.01) | |
| C07D 275/03 | (2006.01) | |
| C07D 277/44 | (2006.01) | |
| C07D 285/135 | (2006.01) | |
| C07D 211/56 | (2006.01) | |

(52) U.S. Cl. ........ 514/336; 514/352; 514/377; 514/380; 514/383; 514/404; 514/363; 514/364; 514/372; 548/364.1; 548/372.5; 548/139; 548/265.4; 548/143; 548/214; 548/246; 546/268.1; 546/309

(58) Field of Classification Search .................. None
See application file for complete search history.

(56) References Cited

U.S. PATENT DOCUMENTS

| | | | |
|---|---|---|---|
| 7,511,013 B2 | 3/2009 | Molino et al. | |
| 7,514,068 B2 | 4/2009 | Tung | |
| 7,521,421 B2 | 4/2009 | Naicker et al. | |
| 7,528,131 B2 | 5/2009 | Persichetti et al. | |
| 7,531,685 B2 | 5/2009 | Czarnik | |
| 7,534,814 B2 | 5/2009 | Ascher et al. | |
| 7,538,189 B2 | 5/2009 | Naicker et al. | |
| 2009/0082471 A1 | 3/2009 | Czarnik | |
| 2009/0088416 A1 | 4/2009 | Czarnik | |
| 2009/0093422 A1 | 4/2009 | Tung et al. | |
| 2009/0105147 A1 | 4/2009 | Masse | |
| 2009/0105307 A1 | 4/2009 | Galley et al. | |
| 2009/0105338 A1 | 4/2009 | Czarnik | |
| 2009/0111840 A1 | 4/2009 | Herold et al. | |
| 2009/0118238 A1 | 5/2009 | Czarnik | |
| 2009/0131363 A1 | 5/2009 | Harbeson | |
| 2009/0131485 A1 | 5/2009 | Liu et al. | |
| 2009/0137457 A1 | 5/2009 | Harbeson | |

FOREIGN PATENT DOCUMENTS

| | | |
|---|---|---|
| EP | 1820504 A1 | 8/2007 |
| WO | WO9507271 A1 | 3/1995 |
| WO | WO9710223 A1 | 3/1997 |
| WO | WO2005099353 A2 | 10/2005 |
| WO | WO2006008754 A1 | 1/2006 |
| WO | WO2010033543 A2 | 3/2010 |

OTHER PUBLICATIONS

Arevalo-Martin A. et al., "Therapeutic Action of Cannabinoids in a Murine Model of Multiple Sclerosis," Journal of Neuroscience, 2003, vol. 23 (7), pp. 2511-2516.
Benito C. et al., "Cannabinoid CB2 Receptors and Fatty Acid Amide Hydrolase Are Selectively Overexpressed in Neuritic Plaque-Associated Glia in Alzheimer's Disease Brains," Journal of Neuroscience, 2003, vol. 23 (35), pp. 11136-11141.
Berge S. M., et al., "Pharmaceutical Salts," J Pharmaceutical Sciences, 1977, 66 (1), 1-19.
Beylot M., et al., "In vivo studies of intrahepatic metabolic pathways," Diabetes Metabolism, 1997, 23 (3), 251-257.
Blagojevic N., et al., "Role of heavy water in Boron Neutron Capture Therapy," in Topics in Dosimetry & Treatment Planning for Neutron Capture Therapy, Advanced Medical Publishing, Madison, WI, 1994, 125-134.
Blake et al., "Studies with deuterated drugs," J. Pharm. Sci., 1975, 64 (3), 367-391.
Bouchard J. F et al., "Contribution of endocannabinoids in the endothelial protection afforded by ischemic preconditioning in the isolated rat heart," Life Sciences, 2003, vol. 72, pp. 1859-1870.
Boyle W. J. et al., "Osteoclast differentiation and activation," Nature, 2003, vol. 423, pp. 337-342.
Brickner S. J., et al., "Synthesis and antibacterial activity of U-100592 and U-100766, two oxazolidinone antibacterial agents for the potential treatment of multidrug-resistant gram-positive bacterial infections," J Med Chem., 1996, 39 (3), 673-679.

(Continued)

*Primary Examiner* — Kamal Saeed
*Assistant Examiner* — Michael Barker
(74) *Attorney, Agent, or Firm* — Nancy J. Gettel; Andrew M. Parial

(57) ABSTRACT

Cannabinoid receptor ligands of formula (I)

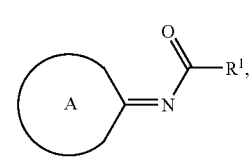

wherein Ring A and $R^1$ are as defined in the specification. Compositions including such compounds, and methods of treating conditions and disorders using such compounds and compositions are also described.

20 Claims, No Drawings

OTHER PUBLICATIONS

Buckley N. E. et al., "Immunomodulation by cannabinoids is absent in mice deficient for the cannabinoid CB receptor," European Journal of Pharmacology, 2000, vol. 396, pp. 141-149.
Carlisle S. J. et al., "Differential expression of the CB2 cannabinoid receptor by rodent macrophages and macrophage-like cells in relation to cell activation," International Immunopharmacology, 2002, vol. 2, pp. 69.
Carrier E. J. et al., "Endocannabinoids in Neuroimmunology and Stress," Current Drug Targets CNS & Neurological Disorders, 2005, vol. 4, pp. 657-665.
Casanova M. L. et al., "Inhibition of skin tumor growth and angiogenesis in vivo by activation of cannabinoid receptors," Journal of Clinical Investigation, 2003, vol. 111, pp. 43-50.
Cichewicz D. L. et al., "Synergistic interactions between cannabinoid and opioid analgesics," Life Sciences, 2004, vol. 74, pp. 1317-1324.
Clayton N., et al., "CB1 and CB2 cannabinoid receptors are implicated in inflammatory pain," Pain, 2002, vol. 96, pp. 253-260.
Czajka D. M., "Effect of deuterium oxide on the reproductive potential of mice," Ann NY Acad Sci, 1960, vol. 84, pp. 770-779.
Czajka D.M., et al., "Physiological effects of deuterium on dogs," Am. J. Physiol., 1961, 201 (2), 357-362.
Filippo C. D. et al., "Cannabinoid CB2 receptor activation reduces mouse myocardial ischemia-reperfusion injury: involvement of cytokine/chemokines and PMN," Journal of Leukocyte Biology, 2004, vol. 75, pp. 453-459.
Foster, A.B., et al., "Deuterium Isotope Effects in the Metabolism of Drugs and Xenobiotics: Implications for Drug Design," Advances in Drug Research, 1985, 14, Academic Press, London, 2-36.
Galiégue et al., "Expression of central and peripheral cannabinoid receptors in human immune tissues and leukocyte subpopulations," European Journal of Biochemistry, 1995, vol. 232, pp. 54-61.
Goodman A. J., et al., "CB2 selective sulfamoyl benzamides: optimization of the amide functionality", Bioorg Med Chem Lett., 2009, 19 (2), 309-313.
Greene T. et al., Protective Groups in Organic Synthesis (3rd ed.), John Wiley & Sons, NY (1999). Table of Contents.
Grotenhermen F. et al., "IACM 2nd Conference on Cannabinoids in Medicine," Expert Opinion in Pharmacotherapy, 2003, vol. 4 (12), pp. 2367-2371.
Hanus L. et al., "HU-308: A specific agonist for CB 2, a peripheral cannabinoid receptor," Proceedings of the National Academy of Science, 1999, vol. 96, pp. 14228-14233.
Hohmann A. G. et al., "Selective Activation of Cannabinoid CB2 Receptors Suppresses Hyperalgesia Evoked by Intradermal Capsaicin," Journal of Pharmacology and Experimental Therapeutics, 2004, vol. 308, pp. 446-453.
Ibrahim M. M. et al., "Activation of CB2 cannabinoid receptors by AM1241 inhibits experimental neuropathic pain: Pain inhibition by receptors not present in the CNS," Proceedings of the National Academy of Science, 2003, vol. 100 (18), pp. 10529-10533.
Ibrahim M. M. et al., "CB2 cannabinoid receptor activation produces antinociception by stimulating peripheral release of endogenous opioids," Proceedings of the National Academy of Science, 2005, vol. 102 (8), pp. 3093-3098.
Ihenetu K. et al., "Inhibition of interleukin-8 release in the human colonic epithelial cell line HT-29 by cannabinoids," European Journal of Pharmacology, 2003, vol. 458, pp. 207-215.
International Search Report for Application No. PCT/US2010/028796, mailed Jul. 16, 2010, 4 pages.
IUPAC Commission on Nomenclature of Organic Chemistry: Rules for the Nomenclature of Organic Chemistry Section E: Stereochemistry, Pure Appl Chem, 1976, 45, 11-30.
Julien B et al., "Antifibrogenic Role of the Cannabinoid Receptor CB2 in the Liver," Gastroenterology, 2005, vol. 128, pp. 742-755.
Karsak M. et al., "Cannabinoid receptor type 2 gene is associated with human osteoporosis," Human Molecular Genetics, 2005, vol. 14 (22), pp. 3389-3396.
Kato et al., "Synthesis of Deuterated Mosapride Citrate," J. Labelled Comp. Radiopharmaceut, 1995, 36 (10), 927-932.
Kushner et al., "Pharmacological uses and perspectives of heavy water and deuterated compounds," Can J Physiol Pharmacol, 1999, vol. 77, pp. 79-88.
Lepicier P. et al., "Endocannabinoids protect the rat isolated heart against ischaemia," British Journal of Pharmacology, 2003, vol. 139, pp. 805-815.
Lizondo J., et al., "Linezolid: Oxazolidinone antibacterial," Drugs of the Future, 1996, 21 (11), 1116-1123.
Lotersztajn S. et al., "Hepatic Fibrosis: Molecular Mechanisms and Drug Targets," Annual Review of Pharmacology and Toxicology, 2005, vol. 45, pp. 605-628.
Malan T. P. et al., "CB2 cannabinoid receptor-mediated peripheral antinociception," Pain, 2001, vol. 93, pp. 239-245.
Mallesham B., et al., "Highly efficient CuI-catalyzed coupling of aryl bromides with oxazolidinones using Buchwald's protocol: a short route to linezolid and toloxatone," Org. Lett., 2003, 5 (7), 963-965.
Maresz K. et al., "Modulation of the cannabinoid CB2 receptor in microglial cells in response to inflammatory stimuli," Journal of Neurochemistry, 2005, vol. 95, pp. 437-445.
Mathison R. et al., "Effects of cannabinoid receptor-2 activation on accelerated gastrointestinal transit in lipopolysaccharide-treated rats," British Journal of Pharmcology, 2004, vol. 142, pp. 1247-1254.
McKallip R. J., et al., "Targeting CB2 cannabinoid receptors as a novel therapy to treat malignant lymphoblastic disease," Blood, 2002, vol. 15 (2), pp. 627-634.
Nackley A. G. et al., "Selective activation of cannabinoid CB2 receptors suppresses spinal fos protein expression and pain behavior in a rat model of inflammation," Neuroscience, 2003, vol. 119, pp. 747-757.
Ni X. et al., "Win 55212-2, a cannabinoid receptor agonist, attenuates leukocyte/endothelial interactions in an experimental autoimmune encephalomyelitis model," Multiple Sclerosis, 2004, vol. 10, pp. 158-164.
Patel J. J. et al., "Inhibition of guinea-pig and human sensory nerve activity and the cough reflex in guinea-pigs by cannabinoid (CB2) receptor activation," British Journal of Pharmacology, 2003, vol. 140, pp. 261-268.
Pertwee R. G., "Cannabinoids and multiple sclerosis," Pharmacology & Therapeutics, 2002, vol. 95, pp. 165-174.
Prescott et al., "Lipid Vesicles as Carriers for Introducing Biologically Active Materials into Cells," Methods in Cell Biology, 1976, Academic Press, 33-71.
Quartilho A. et al., "Inhibition of Inflammatory Hyperalgesia by Activation of Peripheral CB2 Cannabinoid Receptors," Anesthesiology, 2003, vol. 99, pp. 955-960.
Ralston S. H., "Regulation of bone mass, bone loss and osteoclast activity by cannabinoid receptors," Nature Medicine, 2005, vol. 11, pp. 774-779.
Ramirez B. G. et al., "Prevention of Alzheimer's Disease Pathology by Cannabinoids: Neuroprotection Mediated by Blockade of Microglial Activation," Journal of Neuroscience, 2005, vol. 25 (8), pp. 1904-1913.
Sanchez C. et al., "Inhibition of Glioma Growth in Vivo by Selective Activation of the CB2 Cannabinoid Receptor1," Cancer Research, 2001, vol. 61, pp. 5784-5789.
Steffens S. et al., "Low dose oral cannabinoid therapy reduces progression of atherosclerosis in mice," Nature, 2005, vol. 434, pp. 782-786.
Thomson J. F., "Physiological effects of D20 in mammals," Ann. New York Acad. Sci., 1960, 84, 736-744.
Valenzano K. J. et al., "Pharmacological and pharmacokinetic characterization of the cannabinoid receptor 2 agonist, GW405833, utilizing rodent models of acute and chronic pain, anxiety, ataxia and catalepsy," Neuropharmacology, 2005, vol. 48, pp. 658-672.
Warhurst A. C. et al., "Interferon gamma induces differential upregulation of alpha and beta chemokine secretion in colonic epithelial cell lines," Gut, 1998, vol. 42, pp. 208-213.
Wright K. et al., "Differential Expression of Cannabinoid Receptors in the Human Colon: Cannabinoids Promote Epithelial Wound Healing," Gastroenterology, 2005, vol. 129, pp. 437-453.
Yoshihara S. et al., "Cannabinoid Receptor Agonists Inhibit Sensory Nerve Activation in Guinea Pig Airways," American Journal of Respiratory and Critical Care Medicine, 2004, vol. 170, pp. 941-946.
Yoshihara S. et al., "Endogenous Cannabinoid Receptor Agonists Inhibit Neurogenic Inflammations in Guinea Pig Airways," Allergy and Immunology, 2005, vol. 138, pp. 80-87.
Yoshihara S. et al., "The Cannabinoid Receptor Agonist WIN 55212-2 Inhibits Neurogenic Inflammations in Airway Tissues," Journal of Pharmacological Sciences, 2005, vol. 98 (1), pp. 77-82.

COMPOUNDS AS CANNABINOID RECEPTOR LIGANDS

This application claims priority to U.S. Application Ser. No. 61/163,953 filed Mar. 27, 2009, and is hereby incorporated by reference in its entirety.

TECHNICAL FIELD AND BACKGROUND

Compounds that are cannabinoid receptor ligands, compositions comprising such compounds, and methods for treating conditions and disorders using such compounds and compositions are disclosed.

(−)-$\Delta^9$-Tetrahydrocannabinol ($\Delta^9$-THC), the major psychoactive constituent of marijuana, exerts a broad range of effects through its interactions with two cannabinoid (CB) receptor subtypes, $CB_1$ and $CB_2$. $CB_1$ receptors are highly expressed in the central nervous system and to a lesser degree in the periphery in a variety of tissues of the cardiovascular and gastrointestinal systems. By contrast, $CB_2$ receptors are most abundantly expressed in multiple lymphoid organs and cells of the immune system, including spleen, thymus, tonsils, bone marrow, pancreas and mast cells.

The psychotropic effects caused by $\Delta^9$-THC and other nonselective CB agonists are mediated by $CB_1$ receptors. These $CB_1$ receptor-mediated effects, such as euphoria, sedation, hypothermia, catalepsy, and anxiety, have limited the development and clinical utility of nonselective CB agonists. Recent studies have demonstrated that $CB_2$ modulators are analgesic in pre-clinical models of nociceptive and neuropathic pain without causing the adverse side effects associated with $CB_1$ receptor activation. Therefore, compounds that selectively target $CB_2$ receptors are an attractive approach for the development of novel analgesics.

Pain is the most common symptom of disease and the most frequent complaint with which patients present to physicians. Pain is commonly segmented by duration (acute vs. chronic), intensity (mild, moderate, and severe), and type (nociceptive vs. neuropathic). Nociceptive pain is the most well known type of pain, and is caused by tissue injury detected by nociceptors at the site of injury. After the injury, the site becomes a source of ongoing pain and tenderness. This pain and tenderness are considered "acute" nociceptive pain. This pain and tenderness gradually diminish as healing progresses and disappear when healing is complete. Examples of acute nociceptive pain include surgical procedures (post-operative pain) and bone fractures. Even though there can be no permanent nerve damage, "chronic" nociceptive pain results from some conditions when pain extends beyond six months. Examples of chronic nociceptive pain include osteoarthritis, rheumatoid arthritis, and musculoskeletal conditions (e.g., back pain), cancer pain, etc.

Neuropathic pain is defined as "pain initiated or caused by a primary lesion or dysfunction in the nervous system" by the International Association for the Study of Pain. Neuropathic pain is not associated with nociceptive stimulation, although the passage of nerve impulses that is ultimately perceived as pain by the brain is the same in both nociceptive and neuropathic pain. The term neuropathic pain encompasses a wide range of pain syndromes of diverse etiologies. The three most commonly diagnosed pain types of neuropathic nature are diabetic neuropathy, cancer neuropathy, and HIV pain. In addition, neuropathic pain is diagnosed in patients with a wide range of other disorders, including trigeminal neuralgia, post-herpetic neuralgia, traumatic neuralgia, fibromyalgia, phantom limb, as well as a number of other disorders of ill-defined or unknown origin.

Managing the spectrum of pain etiologies remains a major public health problem and both patients and clinicians are seeking improved strategies to effectively manage pain. No currently available therapies or drugs effectively treat all types of nociceptive and neuropathic pain states. The compounds of the present invention are novel $CB_2$ receptor modulators that have utility in treating pain, including nociceptive and neuropathic pain.

The location of $CB_2$ receptors on the surface of immune cells suggests a role for these receptors in immunomodulation and inflammation. Recent studies have demonstrated that $CB_2$ receptor ligands have immunomodulatory and anti-inflammatory properties. Therefore, compounds that interact with $CB_2$ receptors offer a unique pharmacotherapy for the treatment of immune and inflammatory disorders.

SUMMARY OF INVENTION

Provided herein are compounds of formula (I)

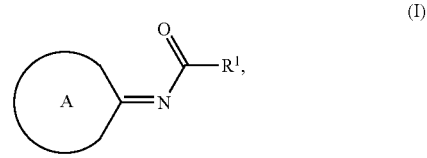

(I)

or pharmaceutically acceptable salts, solvates, prodrugs, salts of prodrugs, or any combinations thereof, wherein $R^1$ is aryl, heteroaryl, heterocycle, cycloalkyl, or cycloalkenyl; each of which is substituted by one $R^x$ group and each is optionally further substituted with 1, 2, 3, or 4 $R^y$ group(s);

$R^x$ is —O—$(CR^{1a}R^{1b})_{q1}$—$N(R^{1m})_2$ or —O-$G^1$;

each $R^y$ is independently $G^{1d}$, alkyl, alkenyl, alkynyl, halogen, haloalkyl, =N—CN, $NO_2$, =N—$OR^f$, —CN, oxo, —$OR^f$, —$OC(O)R^f$, —$OC(O)N(R^f)_2$, —$S(O)_2R^e$, —$S(O)_2N(R^f)_2$, —$C(O)R^f$, —$C(O)OR^f$, —$C(O)N(R^f)_2$, —$N(R^f)_2$, —$N(R^f)C(O)R^f$, —$N(R^f)S(O)_2R^e$, —$N(R^f)C(O)O(R^e)$, —$N(R^f)C(O)N(R^f)_2$, —$N(R^f)S(O)_2N(R^f)_2$, —$(CR^{1c}R^{1d})_{q2}$—$OR^f$, —$(CR^{1c}R^{1d})_{q2}$—$OC(O)R^f$, —$(CR^{1c}R^{1d})_{q2}$—$OC(O)N(R^f)_2$, —$(CR^{1c}R^{1d})_{q2}$—$S(O)_2R^e$, —$(CR^{1c}R^{1d})_{q2}$—$S(O)_2N(R^f)_2$, —$(CR^{1c}R^{1d})_{q2}$—$C(O)R^f$, —$(CR^{1c}R^{1d})_{q2}$—$C(O)OR^f$, —$(CR^{1c}R^{1d})_{q2}$—$C(O)N(O)N(R^f)_2$, —$(CR^{1c}R^{1d})_{q2}$—$N(R)_2$, —$(CR^{1c}R^{1d})_{q2}$—$N(R^f)C(O)R^f$, —$(CR^{1c}R^{1d})_{q2}$—$N(R^f)S(O)_2R^e$, —$(CR^{1c}R^{1d})_{q2}$—$N(R^f)C(O)O(R^e)$, —$(CR^{1c}R^{1d})_{q2}$—$N(R^f)C(O)N(R^f)_2$, —$(CR^{1c}R^{1d})_{q2}$—$N(R^f)S(O)_2N(R^f)_2$, or —$(CR^{1c}R^{1d})_{q2}$—CN;

$R^{1m}$, at each occurrence, is independently, hydrogen or $C_1$-$C_4$ alkyl;

$R^{1a}$, at each occurrence, is independently hydrogen or $C_1$-$C_4$ alkyl;

$R^{1b}$, at each occurrence, is independently hydrogen or $C_1$-$C_4$ alkyl;

$G^1$ is cycloalkyl, cycloalkenyl, aryl, heterocycle, or heteroaryl; each of which is optionally substituted with 1, 2, 3, 4, 5, or 6 substituents independently selected from the group consisting of oxo, alkyl, alkenyl, alkynyl, halogen, haloalkyl, =N—CN, —C(=$NOR^f$)$R^a$, =N—$OR^f$, —CN, $NO_2$, oxo, —$OR^a$, —$OC(O)R^a$, —$OC(O)N(R^b)(R^c)$, —$S(O)R^d$, —$S(O)_2R^d$, —$S(O)_2N(R^b)(R^c)$, —$C(O)R^a$, —$C(O)OR^a$, —$C(O)N(R^b)(R^c)$, —$N(R^b)(R^c)$, —$N(R^c)C(O)R^a$, —$N(R^c)S(O)_2R^d$, —$N(R^c)C(O)O(R^a)$, —$N(R^c)S(O)_2N(R^b)(R^c)$, —$N(R^c)C(O)N(R^b)(R^c)$, —$(CR^{1c}R^{1d})_{q3}$—$OR^a$, —$(CR^{1c}R^{1d})_{q3}$—$OC(O)R^a$, —$(CR^{1c}R^{1d})_{q3}$—$OC(O)N(R^b)(R^c)$, —$(CR^{1c}R^{1d})_{q3}$—$S(O)R^d$, —$(CR^{1c}R^{1d})_{q3}$—$S(O)_2R^d$, —(CR$^{1c}$R$^{1d}$)$_{q3}$—S(O)$_2$N(R$^b$)(R$^c$), —(CR$^{1c}$R$^{1d}$)$_{q3}$—C(O) R$^a$, —(CR$^{1c}$R$^{1d}$)$_{q3}$—C(O)OR$^a$, —(CR$^{1c}$R$^{1d}$)$_{q3}$—C(O)N (R$^b$)(R$^c$), —(CR$^{1c}$R$^{1d}$)$_{q3}$—N(R$^b$)(R$^c$), —(CR$^{1c}$R$^{1d}$)$_{q3}$—N (R$^c$)C(O)R$^a$, —(CR$^{1c}$R$^{1d}$)$_{q3}$—N(R$^c$)S(O)$_2$R$^d$, —(CR$^{1c}$ R$^{1d}$)$_{q3}$—N(R$^c$)C(O)O(R$^a$), —(CR$^{1c}$R$^{1d}$)$_{q3}$—N(R$^c$)S(O)$_2$N (R$^b$)(R$^c$), —(CR$^{1c}$R$^{1d}$)$_{q3}$—N(R$^c$)C(O)N(R$^b$)(R$^c$), and —(CR$^{1c}$R$^{1d}$)$_{q3}$—CN;

R$^a$ and R$^c$, at each occurrence, are each independently hydrogen, alkyl, haloalkyl, —(CR$^{1a}$R$^{1b'}$)$_{q4}$-A$^3$, G$^{1d}$, or —(CR$^{1a}$R$^{1b'}$)$_{q4}$-G$^{1d}$;

R$^b$, at each occurrence, is independently hydrogen, alkyl, haloalkyl, alkoxyalkyl, monocyclic cycloalkyl, —(CR$^{1c}$ R$^{1d}$)$_{q4}$-(monocyclic cycloalkyl), or haloalkoxyalkyl;

R$^d$, at each occurrence, is independently alkyl, haloalkyl, —(CR$^{1a}$R$^{1b'}$)$_{q3}$-A$^3$, G$^{1d}$, or —(CR$^{1a}$R$^{1b'}$)$_{q4}$-G$^{1d}$;

G$^{1d}$, at each occurrence, is independently a monocyclic heterocycle, a monocyclic heteroaryl, a phenyl, a monocyclic cycloalkyl, or a monocyclic cycloalkenyl; optionally substituted with 1, 2, 3, or 4 substituents independently selected from the group consisting of —N(R$^h$)$_2$, —CN, oxo, alkyl, haloalkyl, alkoxy, haloalkoxy, halogen, and —OH;

each occurrence of A$^3$ is independently —C(O)R$^h$, —S(O)$_2$R$^e$, —C(O)N(R$^h$)$_2$, —C(S)N(R$^h$)$_2$, —S(O)$_2$N(R$^h$)$_2$, —C(=NOR$^h$)R$^h$, —N(R$^h$)C(O)R$^h$, —N(R$^h$)C(O)OR$^e$, —N(R$^h$)S(O)$_2$R$^e$, —N(R$^h$)C(O)N(R$^h$)$_2$, —N(R$^h$)S(O)$_2$N (R$^h$)$_2$, —CN, —OR'', or —N(R$^h$)$_2$;

R$^e$, at each occurrence, is independently C$_1$-C$_4$ alkyl, C$_1$-C$_4$ haloalkyl, monocyclic cycloalkyl, monocyclic heterocycle, or —(CR$^{1c}$R$^{1d}$)$_{q4}$-(monocyclic cycloalkyl);

R$^f$, at each occurrence, is independently hydrogen, C$_1$-C$_4$ alkyl, C$_1$-C$_4$ haloalkyl, —(CR$^{1c}$R$^{1d}$)$_{q4}$—OR$^h$, monocyclic heterocycle, monocyclic cycloalkyl, or —(CR$^{1c}$R$^{1d}$)$_{q4}$-(monocyclic cycloalkyl);

R$^h$, at each occurrence, is independently hydrogen, C$_1$-C$_4$ alkyl, C$_1$-C$_4$ haloalkyl, monocyclic heterocycle, monocyclic cycloalkyl, or —(CR$^{1c}$R$^{1d}$)$_{q4}$-(monocyclic cycloalkyl);

Ring A represents formula (a), (b), (c), or (d)

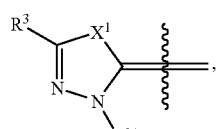
(a)

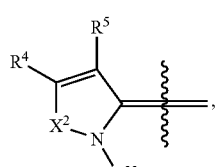
(b)

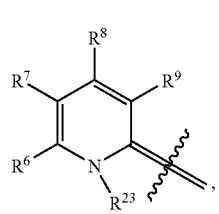
(c)

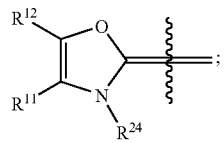
(d)

R$^{21}$, R$^{22}$, R$^{23}$, and R$^{24}$ are each independently alkyl, alkenyl, alkynyl, haloalkyl, —(CR$^{2a}$R$^{2b}$)$_{q5}$—OH, —(CR$^{2a}$R$^{2b}$)$_{q5}$—O-alkyl, —(CR$^{2a}$R$^{2b}$)$_{q5}$—O-haloalkyl, —(CR$^{2a}$R$^{2b}$)$_{q5}$—O-G$^2$a, —(CR$^{2a}$R$^{2b}$)$_{q5}$—O—(CR$^{2c}$R$^{2d}$)$_{q6}$-G$^2$a, —(CR$^{2a}$R$^{2b}$)$_{q6}$—C(O)—R$^a$, —(CR$^{2a}$R$^{2b}$)$_{q6}$—C(O)O(R$^a$), —(CR$^{2a}$R$^{2b}$)$_{q6}$—C(=N—OR$^f$)R$^a$, —(CR$^{2a}$R$^{2b}$)$_{q6}$—SO$_2$—R$^d$, —(CR$^{2a}$R$^{2b}$)$_{q6}$-G$^{2b}$, —(CR$^{2a}$R$^{2b}$)$_{q6}$—C(O)N(R$^b$)(R$^c$), or —(CR$^{2a}$R$^{2b}$)$_{q6}$—CN;

each occurrence of G$^{2a}$ is independently cycloalkyl, heterocycle, aryl, or heteroaryl;

G$^{2b}$ is monocyclic cycloalkyl, monocyclic cycloalkenyl, thienyl, or phenyl; each of which is optionally fused with benzo, monocyclic cycloalkyl, monocyclic cycloalkenyl, monocyclic heterocycle, or monocyclic heteroaryl;

G$^{2a}$ and G$^{2b}$, at each occurrence, are each independently unsubstituted or substituted with 1, 2, 3, 4, 5, or 6 substituents independently selected from the group consisting of oxo, alkyl, halogen, —OH, alkoxy, haloalkoxy, and haloalkyl;

R$^3$, R$^4$, R$^5$, R$^6$, R$^7$, R$^8$, R$^9$, R$^{11}$, and R$^{12}$ are each independently G$^3$, hydrogen, alkyl, alkenyl, alkynyl, —NO$_2$, —CN, halogen, —OR$^h$, —N(R$^h$)$_2$, —C(O)R$^h$, —C(O)O(R$^h$), haloalkyl, —(CR$^{3a}$R$^{3b}$)$_{q7}$—OR$^h$, —(CR$^{3a}$R$^{3b}$)$_{q7}$—N(R$^h$)$_2$, —(CR$^{3a}$R$^{3b}$)$_{q7}$—C(O)R$^h$, or —(CR$^{3a}$R$^{3b}$)$_{q7}$—C(O)O(R$^h$);

G$^3$, at each occurrence, is independently cycloalkyl, cycloalkenyl, aryl, heterocycle or heteroaryl, each of which is independently unsubstituted or substituted with 1, 2, 3, or 4 substituents selected from the group consisting of C$_1$-C$_4$ alkyl, C$_2$-C$_4$ alkenyl, C$_2$-C$_4$ alkynyl, halogen, C$_1$-C$_4$ haloalkyl, =N—CN, =N—OR$^h$, —CN, oxo, —OR$^h$, —OC (O)R$^h$, —OC(O)N(R$^h$)$_2$, —S(O)$_2$R$^e$, —S(O)$_2$N(R$^h$)$_2$, —C(O)R$^h$, —C(O)OR$^h$, —C(O)N(R$^h$)$_2$, —N(R$^h$)$_2$, —N(R$^h$) C(O)R$^h$, —N(R$^h$)S(O)$_2$R$^e$, —N(R$^h$)C(O)O(R$^e$), and —N(R$^h$)C(O)N(R$^h$)$_2$;

R$^{1a'}$, at each occurrence, is independently hydrogen, halogen, C$_1$-C$_4$ alkyl, or C$_1$-C$_4$ haloalkyl;

R$^{1b'}$, at each occurrence, is independently hydrogen, halogen, C$_1$-C$_4$ alkyl, C$_1$-C$_4$ haloalkyl, —OR$^h$, —N(R$^h$)$_2$, —N(R$^h$)C(O)R$^h$, —N(R$^h$)C(O)OR$^e$, or —N(R$^h$)S(O)$_2$R$^e$;

R$^{1c}$, R$^{1d}$, R$^{2a}$, R$^{2b}$, R$^{2c}$, R$^{2d}$, R$^{3a}$, and R$^{3b}$, at each occurrence, are each independently hydrogen, halogen, C$_1$-C$_4$ alkyl, or C$_1$-C$_4$ haloalkyl;

X$^1$ and X$^2$ are each independently O, S, or N(R$^{10}$) wherein R$^{10}$ is alkyl, alkoxyalkyl, haloalkoxyalkyl, or haloalkyl;

q1 and q5, at each occurrence, are each independently 2, 3, or 4;

q2, q3, q4, q6, and q7, at each occurrence, are each independently 1, 2, 3, 4, 5, or 6; and the monocyclic cycloalkyl and the monocyclic heterocycle, as a substituent or as part of a substituent, of R$^b$, R$^e$, R$^f$, and R$^h$, are each independently unsubstituted or substituted with 1, 2, 3, or 4 substituents independently selected from the group consisting of oxo, C$_1$-C$_4$ alkyl, halogen, —OH, C$_1$-C$_4$ alkoxy, C$_1$-C$_4$ haloalkoxy, and C$_1$-C$_4$ haloalkyl;

with the proviso that when G$^1$ is aryl, then R$^{21}$, R$^{22}$, R$^{23}$, and R$^{24}$ are each independently —(CR$^{2a}$R$^{2b}$)$_{q5}$—O-G$^{2a}$, —(CR$^{2a}$R$^{2b}$)$_{q5}$—O—(CR$^{2c}$R$^{2d}$)$_{q6}$-G$^{2a}$, —(CR$^{2a}$R$^{2b}$)$_{q6}$—C (O)—R$^a$, —(CR$^{2a}$R$^{2b}$)$_{q6}$—C(=N—OR$^f$)R$^a$, or —(CR$^{2a}$R$^{2b}$)$_{q6}$—SO$_2$—R$^d$.

Another aspect is related to pharmaceutical compositions comprising therapeutically effective amount of compound(s) described herein or pharmaceutically acceptable salts, solvates, or salts of solvates thereof, in combination with one or more pharmaceutically acceptable carrier(s). Such compositions can be administered in accordance with a method of the invention, typically as part of a therapeutic regimen for treatment or prevention of conditions and disorders related to cannabinoid (CB) receptor subtype $CB_2$. More particularly, the method is useful for treating conditions related to neuropathic pain, nociceptive pain, post-operative pain, osteoarthritis pain, cancer pain, inflammatory pain, cancer pain, lower back pain, eye pain, inflammatory disorders, immune disorders, neurological disorders, cancers of the immune system, respiratory disorders, obesity, diabetes, cardiovascular disorders, or for providing neuroprotection.

Further provided herein are the use of present compounds or pharmaceutically acceptable salts, solvates, or salts of solvates thereof, in the manufacture of a medicament for the treatment of the disease conditions described above, alone or in combination with one or more pharmaceutically acceptable carrier(s), particularly for the treatment of pain such as, but not limited to, neuropathic pain, nociceptive pain, osteoarthritis pain, inflammatory pain, cancer pain, lower back pain, eye pain, and post-operative pain, or combinations thereof.

The compounds, compositions comprising the compounds, and methods for treating or preventing conditions and disorders by administering the compounds are further described herein. These and other objectives of the invention are described in the following paragraphs. These objectives should not be deemed to narrow the scope of the invention.

DETAILED DESCRIPTION

Provided are compounds of formula (I)

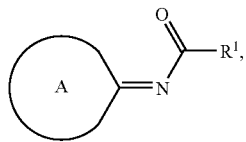

(I)

wherein A and $R^1$ are as defined above in the Summary and below in the Detailed Description. Compositions comprising such compounds and methods for treating conditions and disorders using such compounds and compositions are also disclosed.

In various embodiments, there can be variables that occur more than one time in any substituent or in the compound or any other formulae herein. Definition of a variable on each occurrence is independent of its definition at another occurrence. Further, combinations of variables are permissible only if such combinations result in stable compounds. Stable compounds are compounds that can be isolated from a reaction mixture.

a. Definitions

It is noted that, as used in this specification and the intended claims, the singular form "a," "an," and "the" include plural referents unless the context clearly dictates otherwise. Thus, for example, reference to "a compound" includes a single compound as well as one or more of the same or different compounds, reference to "optional a pharmaceutically acceptable carrier" refers to a single optional pharmaceutically acceptable carrier as well as one or more pharmaceutically acceptable carriers, and the like.

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond. The term "$C_2$-$C_4$ alkenyl" as used herein, means a straight or branched hydrocarbon chain containing from 2 to 4 carbons and containing at least one carbon-carbon double bond. Representative examples of alkenyl include, but are not limited to, ethenyl, 3-methylbut-2-enyl, prop-1-enyl, 2-propenyl, 2-methyl-2-propenyl, 3-butenyl, 3-methylbut-1-enyl, 4-pentenyl, 5-hexenyl, 2-heptenyl, 2-methyl-1-heptenyl, and 3-decenyl.

The term "alkenylene" denotes a divalent group derived from a straight or branched hydrocarbon chain of 2, 3, or 4 carbon atoms and contains at least one carbon-carbon double. Representative examples of alkenylene include, but are not limited to, —CH=CH— and —CH$_2$CH=CH—.

The term "alkoxy" as used herein, means an alkyl group, as defined herein, appended to the parent molecular moiety through an oxygen atom. The term "$C_1$-$C_4$ alkoxy" as used herein, means a $C_1$-$C_4$ alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl" as used herein, means an alkoxy group, as defined herein, appended to the parent molecular moiety through an alkylene group, as defined herein. Representative examples of alkoxyalkyl include, but are not limited to, tert-butoxymethyl, 2-methoxyethyl, 3-methoxy-3-methylbutyl, 2-methoxypropyl, 3-methoxypropyl, 2-ethoxyethyl, 2-methoxyethyl, 3-ethoxypropyl, and methoxymethyl.

The term "alkyl" as used herein, means a saturated, straight or branched hydrocarbon chain containing from 1 to 10 carbon atoms. The terms "$C_1$-$C_4$ alkyl" and "$C_1$-$C_6$ alkyl" as used herein, means a saturated, straight or branched hydrocarbon chain containing from 1 to 4 and from 1 to 6 carbon atoms respectively. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 1-methylbutyl, 2-methylbutyl, 3-methylbutyl, 1,1-dimethylpropyl, 1,2-dimethylpropyl, 2,2-dimethylpropyl, 1-methylpropyl, 1-ethylpropyl, 1,2,2-trimethylpropyl, 2-ethylhexyl, 3-methylhexyl, 2,2-dimethylpentyl, 2,3-dimethylpentyl, n-heptyl, n-octyl, n-nonyl, and n-decyl.

The term "alkylene" means a divalent group derived from a saturated, straight or branched hydrocarbon chain of from 1 to 10 carbon atoms. Representative examples of alkylene include, but are not limited to, —CH$_2$—, —CH(CH$_3$)—, —CH(C$_2$H$_5$)—, —CH(CH(CH$_3$)(C$_2$H$_5$))—, —C(H)(CH$_3$)CH$_2$CH$_2$—, —C(CH$_3$)$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched hydrocarbon chain containing from 2 to 10 carbon atoms and containing at least one carbon-carbon triple bond. The term "$C_2$-$C_4$ alkynyl" as used herein, means a straight or branched hydrocarbon chain containing from 2 to 4 carbon atoms and containing at least one carbon-carbon triple bond. Representative examples of alkynyl include, but are not limited, to acetylenyl, 1-propynyl, 2-propynyl, 1,1-dimethylprop-2-ynyl, 1-propyl-pent-3-ynyl, 3-butynyl, 2-pentynyl, and 1-butynyl.

The term "aryl" as used herein, means phenyl, a bicyclic aryl, or a tricyclic aryl. The bicyclic aryl is naphthyl, or a phenyl fused to a monocyclic cycloalkyl, or a phenyl fused to a monocyclic cycloalkenyl. Representative examples of the bicyclic aryl include, but are not limited to, dihydroindenyl, indenyl, naphthyl, dihydronaphthalenyl, and tetrahydronaphthalenyl (e.g. 1,2,3,4-tetrahydronaphthalen-1-yl). The tricyclic aryl is exemplified by a bicyclic aryl fused to a monocyclic cycloalkyl, or a bicyclic aryl fused to a monocyclic cycloalkenyl, or a bicyclic aryl fused to a phenyl. Representative examples of tricyclic aryls include, but are not limited to, anthracene, phenanthrene, dihydroanthracenyl, fluorenyl, 1,2-dihydroacenaphthylenyl, and tetrahydrophenanthrenyl. The phenyl, bicyclic, and tricyclic aryls are attached to the parent molecular moiety through any carbon atom contained within the phenyl, bicyclic and tricyclic aryls respectively.

The term "cycloalkenyl" as used herein, means a monocyclic or bicyclic ring system containing zero heteroatoms in the ring. The monocyclic cycloalkenyl has three-, four-, five-, six-, seven- or eight carbon atoms and zero heteroatoms. The three or four-membered ring systems have one double bond, the five- or six-membered ring systems have one or two double bonds, and the seven- or eight-membered ring systems have one, two or three double bonds. Representative examples of monocyclic cycloalkenyls include, but are not limited to, 2-cyclohexen-1-yl, 3-cyclohexen-1-yl, 2,4-cyclohexadien-1-yl and 3-cyclopenten-1-yl. Bicyclic cycloalkenyls are exemplified by a monocyclic cycloalkenyl fused to a monocyclic cycloalkyl, or a monocyclic cycloalkenyl fused to a monocyclic cycloalkenyl. Representative examples of bicyclic ring systems include, but are not limited to 3a, 4,5, 6,7,7a-hexahydro-1H-indenyl, 4,5,6,7-tetrahydro-3aH-indene, and octahydronaphthalenyl. The cycloalkenyl groups are appended to the parent molecular moiety through any substitutable carbon atom within the groups, and can contain one or two alkylene bridges of 1, 2, 3, or 4 carbon atoms, wherein each bridge links two non-adjacent atoms within the groups.

The term "cycloalkyl" as used herein, means a monocyclic, or a bicyclic cycloalkyl, or a spirocyclic cycloalkyl. The term "$C_3$-$C_6$ cycloalkyl" as used herein, means a monocyclic cycloalkyl having 3, 4, 5, or 6 carbon atoms and zero heteroatom in the ring. The monocyclic cycloalkyl is a carbocyclic ring system containing 3, 4, 5, 6, 7, or 8 carbon atoms and zero heteroatoms as ring atoms, and zero double bonds. Examples of monocyclic cycloalkyls include cyclopropyl, cyclobutyl, cyclopentyl, cyclohexyl, cycloheptyl, and cyclooctyl. Bicyclic cycloalkyl is exemplified by a monocyclic cycloalkyl fused to a monocyclic cycloalkyl. Representative examples of bicyclic cycloalkyls include, but are not limited to, bicyclo[4.1.0]heptane, bicyclo[6.1.0]nonane, octahydroindene, and decahydronaphthalene. The monocyclic and the bicyclic cycloalkyl groups can contain one or two alkylene bridges of 1, 2, 3, or 4 carbon atoms, wherein each bridge links two non-adjacent atoms within the groups. Examples of such bridged cycloalkyls include, but are not limited to, 6,6-dimethylbicyclo[3.1.1]heptyl (including 6,6-dimethylbicyclo[3.1.1]hept-2-yl), bicyclo[2.2.1]heptyl, bicyclo[3.1.1]heptyl, bicyclo[2.2.2]octyl, bicyclo[3.3.1]nonyl, adamantyl(tricyclo[3.3.1.1$^{3,7}$]decane), and noradamantyl(octahydro-2,5-methanopentalene). Spirocyclic cycloalkyl is exemplified by a monocyclic or a bicyclic cycloalkyl, wherein two of the substituents on the same carbon atom of the ring, together with said carbon atom, form a 4-, 5-, or 6-membered monocyclic cycloalkyl. An example of a spirocyclic cycloalkyl is spiro[2.5]octane. The monocyclic, bicyclic, and spirocyclic cycloalkyl groups can be appended to the parent molecular moiety through any substitutable carbon atom of the groups.

The term "halo" or "halogen" as used herein, means —Cl, —Br, —I, or —F.

The term "haloalkoxy" as used herein, means an alkoxy group, as defined herein, in which one, two, three, four, five, or six hydrogen atoms are replaced by halogen. The term "$C_1$-$C_4$ haloalkoxy" as used herein, means a $C_1$-$C_4$ alkoxy group, as defined herein, in which one, two, three, four, five, or six hydrogen atoms are replaced by halogen. Representative examples of haloalkoxy include, but are not limited to, trifluoromethoxy, difluoromethoxy, 2,2,2-trifluoroethoxy, 2,2-difluoroethoxy, 2-fluoroethoxy, and pentafluoroethoxy.

The term "haloalkoxyalkyl" as used herein, means a haloalkoxy group, as defined herein, appended to the parent molecular moiety through an alkylene group, as defined herein.

The term "haloalkyl" as used herein, means an alkyl group, as defined herein, in which one, two, three, four, five, six, or seven hydrogen atoms are replaced by halogen. The term "$C_1$-$C_4$ haloalkyl" as used herein, means a $C_1$-$C_4$ alkyl group, as defined herein, in which one, two, three, four, five, six, or seven hydrogen atoms are replaced by halogen. Representative examples of haloalkyl include, but are not limited to, chloromethyl, 2-fluoroethyl, 2-fluoropropyl, 2-fluoro-1-methylethyl, 2,2-difluoroethyl, trifluoromethyl, 2,2,2-trifluoroethyl, 2,2,2-trifluoro-1,1-dimethylethyl, difluoromethyl, 3-fluoro-3-methylbutyl, 3,3,3-trifluoropropyl, pentafluoroethyl, 2-chloro-3-fluoropentyl, and 2-iodoethyl.

The term "heteroaryl," as used herein, means a monocyclic heteroaryl or a bicyclic heteroaryl. The monocyclic heteroaryl is a 5- or 6-membered ring containing at least one heteroatom independently selected from the group consisting of O, N, and S. The 5-membered ring contains two double bonds and one, two, three, or four heteroatoms. The 6-membered ring contains three double bonds and one, two, three, or four heteroatoms. Representative examples of monocyclic heteroaryl include, but are not limited to, furanyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl is exemplified by a monocyclic heteroaryl fused to phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryls include, but are not limited to, benzofuranyl, benzoxadiazolyl, 1,3-benzothiazolyl, benzimidazolyl, benzodioxolyl, benzothienyl, chromenyl, cinnolinyl, furopyridine, indolyl, indazolyl, isoindolyl, isoquinolinyl, naphthyridinyl, oxazolopyridine, quinolinyl (e.g. quinolin-8-yl), and thienopyridinyl. The monocyclic and the bicyclic heteroaryl groups are connected to the parent molecular moiety through any substitutable carbon atom or any substitutable nitrogen atom contained within the groups. The nitrogen and sulfur heteroatoms of the heteroaryl rings can optionally be oxidized, and are contemplated within the scope of the invention.

The term "heterocycle" or "heterocyclic" as used herein, means a monocyclic heterocycle, a bicyclic heterocycle, or a spirocyclic heterocycle ring system containing at least one heteroatom in the ring. The monocyclic heterocycle is a 3-, 4-5-, 6-, 7-, or 8-membered monocyclic ring containing at least one heteroatom independently selected from the group consisting of O, N, and S. The 3- or 4-membered ring contains 1 heteroatom selected from the group consisting of O, N and S, and optionally one double bond. The 5-membered ring contains zero or one double bond, and one, two or three heteroatoms in the ring selected from the group consisting of O, N and S. The 6-, 7-, or 8-membered ring contains zero, one, or two double bonds, and one, two, or three heteroatoms in the ring selected from the group consisting of O, N and S. Representative examples of monocyclic heterocycles include, but are not limited to, azetidinyl (e.g. azetidin-3-yl), azepanyl, aziridinyl, diazepanyl, 1,3-dioxanyl, 1,4-dioxanyl, 1,3-dioxolanyl, 4,5-dihydroisoxazol-5-yl, 3,4-dihydropyran-6-yl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl (e.g. pyrrolidin-3-yl), tetrahydrofuranyl, tetrahydropyranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is exemplified by a monocyclic heterocycle fused to a phenyl group, or a monocyclic heterocycle fused to a monocyclic cycloalkyl group, or a monocyclic heterocycle fused to a monocyclic cycloalkenyl group, or a monocyclic heterocycle fused to a monocyclic heterocycle group. Non-limiting examples of bicyclic heterocycle include 1,3-benzodioxol-4-yl, 1,3-benzodithiolyl, 2,3-dihydro-1,4-benzodioxinyl, 2,3-dihydrobenzofuranyl (e.g 2,3-dihydro-1-benzofuran-7-yl), 2,3-dihydro-1-benzothienyl, 2,3-dihydro-1H-indolyl, and 1,2,3,4-tetrahydroquinolinyl. Spirocyclic heterocycle means a monocyclic or bicyclic heterocycle ring wherein two substituents on the same carbon atom, together with said carbon atom, form a 4-, 5-, or 6-membered monocyclic cycloalkyl. One example of a spiroheterocycle is 5-oxaspiro[3,4]octane. The heterocycle groups are connected to the parent molecular moiety through any substitutable carbon atom or any substitutable nitrogen atom contained within the group. The monocyclic or bicyclic heterocycle groups can contain an alkenylene bridge of 2, 3, or 4 carbon atoms, or can contain one or two alkylene bridges of 1, 2, 3, or 4 carbon atoms, or combinations thereof, wherein each bridge links two non-adjacent carbon atoms within the groups. Examples of such bridged heterocycles include, but are not limited to, oxaadamantane (2-oxatricyclo[3.3.1.1$^{3,7}$]decane), octahydro-2,5-epoxypentalene, hexahydro-2H-2,5-methanocyclopenta[b]furan, hexahydro-1H-1,4-methanocyclopenta[c]furan, oxabicyclo[2.2.1]heptane and 2,4-dioxabicyclo[4.2.1]nonane. The nitrogen and sulfur heteroatoms in the heterocycle rings can optionally be oxidized and the nitrogen atoms can optionally be quarternized.

The term "hydroxyl" or "hydroxy" means an OH group.

The term "heteroatom" as used herein, means a nitrogen, oxygen, or sulfur atom.

The term "oxo" means =O.

"Treatment" or "treating" pain includes acute or chronic pain and refers to: (1) preventing pain, i.e. causing pain not to develop or occur with less intensity in a subject that can be exposed or predisposed to pain but does not yet experience or display pain, (2) inhibiting pain, i.e., arresting the development or reversing pain, or (3) relieving pain, i.e., decreasing the amount of pain experienced by the subject.

The term "subject" includes animals such as mammals, including, but not limited to, primates (e.g., humans), cows, sheep, goats, horses, dogs, cats, rabbits, rats, mice and the like. In preferred embodiments, the subject is a human.

b. Compounds

CB$_2$ ligands have formula (I) as described above.

Particular values of variable groups in compounds of formula (I) are as follows. Such values can be used where appropriate with any of the other values, definitions, claims or embodiments defined hereinbefore or hereinafter.

In compounds of formula (I), $R^1$ has values as disclosed in the Summary.

In certain embodiments, $R^1$ is aryl. An example of R1 is aryl include, but not limited to, phenyl, naphthyl, and tetrahydronaphthalenyl, each of which is substituted as described in the Summary.

In certain embodiments, $R^1$ is phenyl, substituted as described in the Summary, for example, $R^1$ is formula (I)

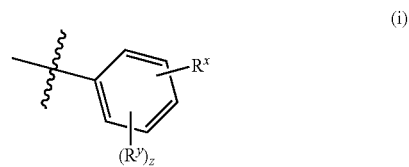

(i)

wherein z is 0, 1, 2, 3, or 4, and $R^x$ and $R^y$ are as described generally in the Summary and embodiments hereinafter.

Thus, included herein are compounds of formula (I-i)

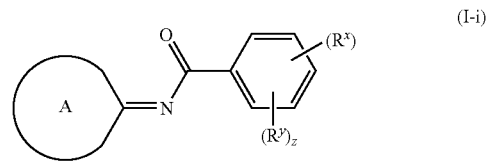

(I-i)

wherein z is 0, 1, 2, 3, or 4, Ring A, $R^x$, and $R^y$ are each described generally in the Summary and in embodiments herein.

In certain embodiments, z is 0, 1, or 2. In other embodiments, z is 0 or 1.

In certain embodiments, $R^1$ is formula (I) wherein z is 1, for example, such as those represented by formula (ii)

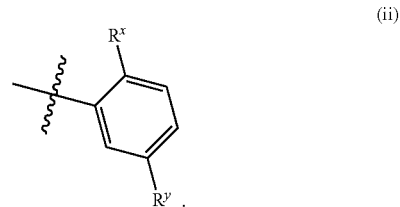

(ii)

Thus, included herein are certain compounds wherein $R^1$ is formula (ii), as represented by formula (I-ii)

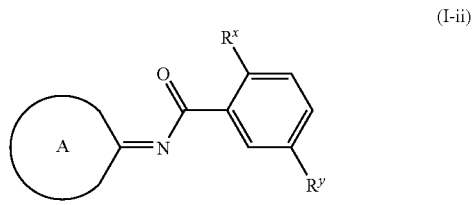

(I-ii)

wherein Ring A, $R^x$, and $R^y$ are each described generally in the Summary and in embodiments herein.

In yet other embodiments, $R^1$ is formula (iii)

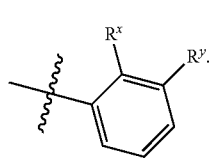
(iii)

Compounds containing $R^1$ having formula (iii) are represented by formula (I-iii)

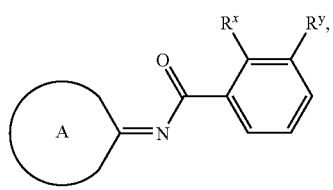
(I-iii)

wherein Ring A, $R^x$, and $R^y$ are each described generally in the Summary and in embodiments herein.

In certain embodiments, $R^1$ is substituted heteroaryl (such as, but not limited thereto, substituted quinolinyl).

In certain embodiments, $R^1$ is substituted heterocycle.

In other embodiments, $R^1$ is substituted cycloalkyl or substituted cycloalkenyl.

$R^x$ in formula (I), (I-i), (I-ii), and (I-iii) has values as generally described in the Summary. In certain embodiments, $R^x$ is, for example, —O—$(CR^{1a}R^{1b})_{q1}$—$N(R^{1m})_2$, wherein $R^{1a}$, $R^{1b}$, q1, and $R^{1m}$ are as described in the Summary and in embodiments herein. For example, in certain compounds of formula (I), (I-i), (I-ii), and (I-iii), $R^{1a}$ and $R^{1b}$ are hydrogen or $C_1$-$C_4$ alkyl (e.g. methyl, ethyl). Each $R^{1m}$, for example, is hydrogen or $C_1$-$C_4$ alkyl such as, but not limited to, tert-butyl.

In other embodiments, $R^x$ is, for example, —O-$G^1$. In certain embodiments, $G^1$ is monocyclic heterocycle, optionally substituted as described in the Summary. For example, $G^1$ is azetidinyl, pyrrolidinyl, piperidinyl, piperazinyl, tetrahydrofuranyl, tetrahydropyranyl, or morpholinyl, each of which is optionally substituted as described in the Summary and herein. In certain embodiments, $G^1$ is optionally substituted azetidinyl or optionally substituted pyrrolidinyl. In certain embodiments, $G^1$ is azetidinyl or pyrrolidinyl, each of which is optionally substituted with one or two substituents selected from the group consisting of alkyl and haloalkyl. In certain embodiments, $G^1$ is optionally substituted azetidinyl.

$R^y$ has values as generally described in the Summary and herein. In certain embodiments, each occurrence of $R^y$, if present, is independently $C_1$-$C_4$ alkyl such as, but not limited to, methyl, —CN, haloalkyl (e.g. trifluoromethyl and the like) —OH, —O($C_1$-$C_4$ alkyl), or halogen. In other embodiments, $R^y$, at each occurrence, is independently fluoro, chloro, bromo, —CN, or trifluoromethyl. In yet other embodiments, $R^y$ is haloalkyl (e.g. trifluoromethyl).

Ring A of formula (I) is described generally in the Summary and in embodiments herein.

In certain embodiments, ring A is formula (a)

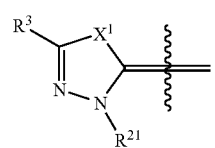
(a)

wherein $R^3$, $X^1$, and $R^{21}$ are as described in the Summary and in embodiments herein.

Examples of compounds include, but are not limited to, those wherein $X^1$ is S.

In conjunction with any of the embodiments herein above and below, examples of $R^3$ include, but are not limited to, alkyl (e.g. $C_1$-$C_4$ alkyl such as, but not limited to, methyl, isopropyl, tert-butyl), alkenyl, alkynyl, haloalkyl (e.g. 2,2,2-trifluoro-1,1-dimethylethyl), or $G^3$ (e.g. optionally substituted $C_3$-$C_6$ cycloalkyl). Particular examples of $R^3$ include, but are not limited to, $C_1$-$C_4$ alkyl (such as, but not limited to, methyl, isopropyl, tert-butyl), alkynyl (e.g. 1,1-dimethylprop-2-ynyl), haloalkyl (e.g. 2,2,2-trifluoro-1,1-dimethylethyl and the like), and optionally substituted $C_3$-$C_6$ cycloalkyl (e.g. cyclopropyl, and cyclobutyl, wherein the cyclopropyl and cyclobutyl are each independently unsubstituted or substituted as described in the Summary and herein below). Examples of the optional substituents of cycloalkyl include, but are not limited to, alkyl (e.g. $C_1$-$C_4$ alkyl such as, but not limited to, methyl, ethyl), haloalkyl (e.g. trifluoromethyl), and halogen (e.g. F, Cl, Br).

In other embodiments, ring A is formula (b)

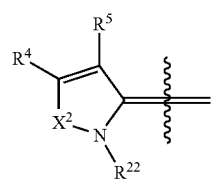
(b)

wherein $R^4$, $R^5$, $R^{22}$, and $X^2$ are as defined in the Summary and in embodiments herein.

In conjunction with any of the embodiments herein above and below, examples of $R^4$ include, but are not limited to, alkyl (e.g. $C_1$-$C_4$ alkyl such as, but not limited to, tert-butyl) or optionally substituted $C_3$-$C_6$ cycloalkyl. For example, $R^4$ is tert-butyl or optionally substituted cyclopropyl. In certain embodiments, $R^4$ is tert-butyl.

In conjunction with any of the embodiments herein above and below, $R^5$, for example, is hydrogen, alkyl, or halogen. In certain embodiments, $R^5$ is hydrogen or halogen (e.g. Br). In certain embodiments, $R^5$ is hydrogen.

In certain embodiments, $X^2$ is O.

In yet other embodiments, $X^2$ is $N(R^{10})$ wherein $R^{10}$ is as disclosed in the Summary and herein. For example, in conjunction with any of the above or below embodiments, $R^{10}$ is $C_1$-$C_4$ alkyl such as, but not limited to, methyl.

Yet other embodiments direct to compounds of formula (I) wherein ring A is formula (c)

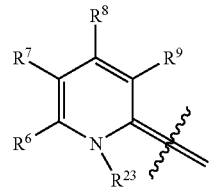

wherein $R^6$, $R^7$, $R^8$, $R^9$ and $R^{23}$ are as defined in the Summary and embodiments herein.

$R^6$ and $R^9$ are, for example, hydrogen.

$R^7$ and $R^8$ are, for example, each independently hydrogen or $C_1$-$C_4$ alkyl such as, but not limited to, methyl, ethyl, tert-butyl, and the like.

Yet still other embodiments provide compounds wherein ring A is formula (d)

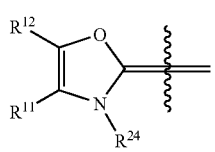

wherein $R^{11}$, $R^{12}$, and $R^{24}$ are as defined in the Summary.

In conjunction with any one of the above or below embodiments, $R^{11}$ and $R^{12}$, for example, are each independently hydrogen, halogen, or alkyl (e.g. $C_1$-$C_4$ alkyl). For example, $R^{12}$ is alkyl such as, but not limited to, tert-butyl, and $R^{11}$ is hydrogen.

$R^{21}$, $R^{22}$, $R^{23}$, and $R^{24}$ in formula (a), (b), (c), and (d) are as described generally in the Summary and in embodiments herein. For example, in certain embodiments, $R^{21}$, $R^{22}$, $R^{23}$ and $R^{24}$ are each independently alkyl (e.g. $C_1$-$C_6$ alkyl such as, but not limited to, n-propyl, sec-butyl, n-butyl, n-pentyl), haloalkyl, $-(CR^{2a}R^{2b})_{q4}-OH$, $-(CR^{2a}R^{2b})_{q4}-O$-alkyl (such as, but not limited to, 3-methoxypropyl), $-(CR^{2a}R^{2b})_{q4}-O$-haloalkyl, or $-(CR^{2a}R^{2b})_{q5}-G^{2b}$. In certain embodiments, $R^{21}$, $R^{22}$, $R^{23}$, and $R^{24}$ are each independently alkyl (e.g. $C_1$-$C_6$ alkyl such as, but not limited to, n-propyl, sec-butyl, n-butyl, n-pentyl), haloalkyl, or $-(CR^{2a}R^{2b})_{q5}-G^{2b}$. In certain embodiments, $R^{21}$, $R^{22}$, $R^{23}$, and $R^{24}$ are each independently alkyl. In yet other embodiments, $R^{21}$, $R^{22}$, $R^{23}$, and $R^{24}$ are each independently $-(CR^{2a}R^{2b})_{q5}-G^{2b}$. $R^{2a}$, $R^{2b}$, q4, q5, and $G^{2b}$ are as described in the Summary and in embodiments herein. In the embodiments wherein $R^{21}$, $R^{22}$, $R^{23}$, and $R^{24}$ are each independently $-(CR^{2a}R^{2b})_{q5}-G^{2b}$, examples of $R^{2a}$ and $R^{2b}$, are each independently hydrogen or $C_1$-$C_4$ alkyl; in certain embodiments, q5 is 1; $G^{2b}$, for example, is optionally substituted monocyclic cycloalkyl such as, but not limited to, cyclopropyl, cyclobutyl, cyclopentyl, each of which is optionally substituted as described in the Summary. In certain embodiments, $G^{2b}$, for example, is unsubstituted. In certain embodiments, $G^{2b}$ is substituted with one or two substituents selected from the group consisting of alkyl (e.g. methyl), oxo, —OH, and halogen.

It is appreciated that compounds of formula (I), (I-i), (I-ii), and (I-iii) with combinations of the above embodiments, including particular, more particular and preferred embodiments are contemplated.

Accordingly, one aspect relates to a group of compounds of formula (I), (I-i), (I-ii), and (I-iii) wherein $R^x$ is —O—$(CR^{1a}R^{1b})_{q1}$—$N(R^{1m})_2$, and Ring A is formula (a).

Another aspect provides a group of compounds of formula (I), (I-i), (I-ii), and (I-iii) wherein $R^x$ is —O-$G^1$ and Ring A is formula (a).

Another aspect relates to a group of compounds of formula (I), (I-i), (I-ii), and (I-iii) wherein $R^x$ is —O—$(CR^{1a}R^{1b})_{q1}$—$N(R^{1m})_2$, Ring A is formula (a), and X is S.

Another aspect provides a group of compounds of formula (I), (I-i), (I-ii), and (I-iii) wherein $R^x$ is —O-$G^1$, Ring A is formula (a), and $X^1$ is S.

Another aspect provides a group of compounds of formula (I), (I-i), (I-ii), and (I-iii) wherein $R^x$ is —O—$(CR^{1a}R^{1b})_{q1}$—$N(R^{1m})_2$, and Ring A is formula (b).

Another aspect provides a group of compounds of formula (I), (I-i), (I-ii), and (I-iii) wherein $R^x$ is —O-$G^1$ and Ring A is formula (b).

Another aspect provides a group of compounds of formula (I), (I-i), (I-ii), and (I-iii) wherein $R^x$ is —O—$(CR^{1a}R^{1b})_{q1}$—$N(R^{1m})_2$, Ring A is formula (b), and $X^2$ is O.

Another aspect provides a group of compounds of formula (I), (I-i), (I-ii), and (I-iii) wherein $R^x$ is —O-$G^1$, Ring A is formula (b), and $X^2$ is O.

Yet another aspect provides a group of compounds of formula (I), (I-i), (I-ii), and (I-iii) wherein $R^x$ is —O—$(CR^{1a}R^{1b})_{q1}$—$N(R^{1m})_2$, Ring A is formula (b), and $X^2$ is $N(R^{10})$.

Yet another aspect provides a group of compounds of formula (I), (I-i), (I-ii), and (I-iii) wherein $R^x$ is —O-$G^1$, Ring A is formula (b), and $X^2$ is $N(R^{10})$.

Yet another aspect provides a group of compounds of formula (I), (I-i), (I-ii), and (I-iii) wherein $R^x$ is —O—$(CR^{1a}R^{1b})_{q1}$—$N(R^{1m})_2$, Ring A is formula (b), $X^2$ is $N(R^{10})$, $R^4$ is alkyl or optionally substituted $C_3$-$C_6$ cycloalkyl, and $R^5$ is hydrogen, alkyl, or halogen.

Yet another aspect provides a group of compounds of formula (I), (I-i), (I-ii), and (I-iii) wherein $R^x$ is —O-$G^1$, Ring A is formula (b), $X^2$ is $N(R^{10})$, $R^4$ is alkyl or optionally substituted $C_3$-$C_6$ cycloalkyl, and $R^5$ is hydrogen, alkyl, or halogen.

A further aspect provides a group of compounds of formula (I), (I-i), (I-ii), and (I-iii) wherein $R^x$ is —O—$(CR^{1a}R^{1b})_{q1}$—$N(R^{1m})_2$, and Ring A is formula (c).

A further aspect provides a group of compounds of formula (I), (I-i), (I-ii), and (I-iii) wherein $R^x$ is —O-$G^1$ and Ring A is formula (c).

A further aspect provides a group of compounds of formula (I), (I-i), (I-ii), and (I-iii) wherein $R^x$ is —O—$(CR^{1a}R^{1b})_{q1}$—$N(R^{1m})_2$, Ring A is formula (c), $R^6$ and $R^9$ are hydrogen, $R^7$ and $R^8$ are each independently hydrogen or $C_1$-$C_4$ alkyl.

Still a further aspect provides a group of compounds of formula (I), (I-i), (I-ii), and (I-iii) wherein $R^x$ is —O-$G^1$, Ring A is formula (c), $R^6$ and $R^9$ are hydrogen, $R^7$ and $R^8$ are each independently hydrogen or $C_1$-$C_4$ alkyl.

Yet a further aspect provides a group of compounds of formula (I), (I-i), (I-ii), and (I-iii) wherein $R^x$ is —O—$(CR^{1a}R^{1b})_{q1}$—$N(R^{1m})^2$ and Ring A is formula (d).

Yet a further aspect provides a group of compounds of formula (I), (I-i), (I-ii), and (I-iii) wherein $R^x$ is —O-$G^1$ and Ring A is formula (d).

Yet a further aspect provides a group of compounds of formula (I), (I-i), (I-ii), and (I-iii) wherein $R^x$ is —O—$(CR^{1a}R^{1b})_{q1}$—$N(R^{1m})_2$, Ring A is formula (d), $R^{11}$ and $R^{12}$, for example, are each independently hydrogen, halogen, or alkyl.

Yet a further aspect provides a group of compounds of formula (I), (I-i), (I-ii), and (I-iii) wherein $R^x$ is —O-$G^1$, Ring A is formula (d), $R^{11}$ and $R^{12}$, for example, are each independently hydrogen, halogen, or alkyl.

Within each group of compounds described above, $R^1$, $R^{21}$, $R^{22}$, $R^{23}$, $R^{24}$, $R^3$, $R^4$, $R^5$, $R^6$, $R^7$, $R^8$, $R^9$, $R^{10}$, $R^{11}$, $R^{12}$, $X^1$, $X^2$, $R^y$, $R^{1a}$, $R^{1b}$, $R^{1m}$, q1, $G^1$, and z, when present, have values as disclosed in the Summary and the Detailed Description.

Thus, of each groups of compounds of formula (I), (I-i), (I-ii), and (I-iii), as described in the preceding paragraphs, examples of a subgroup include, but are not limited to, those wherein $R^{21}$, $R^{22}$, $R^{23}$, and $R^{24}$ are each independently alkyl (e.g. $C_1$-$C_6$ alkyl such as, but not limited to, n-propyl, sec-butyl, n-butyl, n-pentyl), haloalkyl, —$(CR^{2a}R^{2b})_{q4}$—OH, —$(CR^{2a}R^{2b})_{q4}$—O-alkyl (such as, but not limited to, 3-methoxypropyl), —$(CR^{2a}R^{2b})_{q4}$—O-haloalkyl, or —$(CR^{2a}R^{2b})_{q5}$-$G^{2b}$ wherein $R^{2a}$, $R^{2b}$, q4, q5, and $G^{2b}$ are as described in the Summary and Detailed Description sections.

Examples of another subgroup of compounds of formula (I), (I-i), (I-ii), and (I-iii) include, but are not limited to, those wherein $R^{21}$, $R^{22}$, $R^{23}$, and $R^{24}$ are each independently alkyl (e.g. $C_1$-$C_6$ alkyl such as, but not limited to, n-propyl, sec-butyl, n-butyl, n-pentyl), haloalkyl, or —$(CR^{2a}R^{2b})_{q5}$-$G^{2b}$ wherein $R^{2a}$, $R^{2b}$, q5, and $G^{2b}$ are as described in the Summary and Detailed Description sections.

Examples of yet another subgroup of compounds of formula (I), (I-i), (I-ii), and (I-iii) include, but are not limited to, those wherein $R^{21}$, $R^{22}$, $R^{23}$, and $R^{24}$ are each independently alkyl (e.g. $C_1$-$C_6$ alkyl such as, but not limited to, n-propyl, sec-butyl, n-butyl, n-pentyl) or —$(CR^{2a}R^{2b})_{q5}$-$G^{2b}$ and $G^{2b}$ is optionally substituted monocyclic cycloalkyl, wherein $R^{2a}$, $R^{2b}$, and q5 are as described in the Summary and Detailed Description sections.

Examples of yet another subgroup of compounds of formula (I), (I-i), (I-ii), and (I-iii) include, but are not limited to, those wherein $R^{21}$, $R^{22}$, $R^{23}$, and $R^{24}$ are each independently alkyl (e.g. $C_1$-$C_6$ alkyl such as, but not limited to, n-propyl, sec-butyl, n-butyl, n-pentyl).

Examples of yet another subgroup of compounds of formula (I), (I-i), (I-ii), and (I-iii) include, but are not limited to, those wherein $R^{21}$, $R^{22}$, $R^{23}$, and $R^{24}$ are each independently —$(CR^{2a}R^{2b})_{q5}$-$G^{2b}$ wherein $R^{2a}$, $R^{2b}$, q5, and $G^{2b}$ are as described in the Summary and Detailed Description sections.

Examples of still another subgroup of compounds of formula (I), (I-i), (I-ii), and (I-iii) include, but are not limited to, those wherein $R^{21}$, $R^{22}$, $R^{23}$, and $R^{24}$ are each independently alkyl (e.g. $C_1$-$C_6$ alkyl such as, but not limited to, n-propyl, n-butyl, n-pentyl) or —$(CR^{2a}R^{2b})_{q5}$-$G^{2b}$, $G^{2b}$ is optionally substituted monocyclic cycloalkyl, z is 1, and $R^y$ is haloalkyl, wherein $R^{2a}$, $R^{2b}$, and q5 are as described in the Summary and Detailed Description sections.

Specific embodiments of compounds contemplated include, but are not limited to:

2-[2-(tert-butylamino)ethoxy]-N-[(3E)-5-tert-butyl-2-(cyclopropylmethyl)-1-methyl-1,2-dihydro-3H-pyrazol-3-ylidene]-5-(trifluoromethyl)benzamide;

2-[(1-tert-butylazetidin-3-yl)oxy]-N-[(3E)-5-tert-butyl-2-(cyclopropylmethyl)-1-methyl-1,2-dihydro-3H-pyrazol-3-ylidene]-5-(trifluoromethyl)benzamide;

2-[(1-tert-butylazetidin-3-yl)oxy]-N-[(2Z)-3-butyl-5-tert-butyl-1,3,4-thiadiazol-2(3H)-ylidene]-5-(trifluoromethyl)benzamide;

2-[2-(tert-butylamino)ethoxy]-N-[(3E)-2-butyl-5-tert-butyl-1-methyl-1,2-dihydro-3H-pyrazol-3-ylidene]-5-(trifluoromethyl)benzamide;

2-[2-(tert-butylamino)ethoxy]-N-[3E)-5-tert-butyl-2-(cyclobutylmethyl)-1-methyl-1,2-dihydro-3H-pyrazol-3-ylidene]-5-(trifluoromethyl)benzamide; and N-[(3E)-5-tert-butyl-2-(cyclobutylmethyl)-1-methyl-1,2-dihydro-3H-pyrazol-3-ylidene]-2-{[(3S)-1-methylpyrrolidin-3-yl]oxy}-5-(trifluoromethyl)benzamide;

or pharmaceutically acceptable salts, solvates, or salts of solvates thereof.

Compounds of the present application can exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

It can be appreciated that two or more asymmetric centers can be present in the present compounds, hence several diastereomers and enantiomers of the exemplified structures can often be possible, and that pure diastereomers and enantiomers represent preferred embodiments. It is intended that pure diasteromers, pure enantiomers, and mixtures thereof, are within the scope of the invention.

Various stereoisomers (including enantiomers and diastereomers) and mixtures thereof (including racemates) are contemplated. Individual stereoisomers of present compounds can be prepared synthetically from commercially available starting materials that contain asymmetric or chiral centers or by preparation of racemic mixtures followed by resolution of the individual stereoisomer using methods that are known to those of ordinary skill in the art. Examples of resolution are, for example, (i) attachment of a mixture of enantiomers to a chiral auxiliary, separation of the resulting mixture of diastereomers by recrystallization or chromatography, followed by liberation of the optically pure product; or (ii) separation of the mixture of enantiomers or diastereomers on chiral chromatographic columns.

Geometric isomers can exist in the present compounds. Thus various geometric isomers and mixtures thereof resulting from the disposition of substituents around a carbon-carbon double bond, a carbon-nitrogen double bond, a cycloalkyl group, or a heterocycle group are part of the invention. Substituents around a carbon-carbon double bond or a carbon-nitrogen bond are designated as being of Z or E configuration and substituents around a cycloalkyl or a heterocycle are designated as being of cis or trans configuration.

Within the present application it is to be understood that compounds disclosed herein can exhibit the phenomenon of tautomerism.

Though structural representations within this specification can show only one of the possible tautomeric or stereoisomeric forms, it is to be understood that the invention encompasses any tautomeric or stereoisomeric form, and mixtures thereof, and is not to be limited merely to any one tautomeric or stereoisomeric form utilized within the naming of the compounds or drawings.

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to, $^2H$, $^3H$, $^{13}C$, $^{14}C$, $^{15}N$, $^{18}O$, $^{32}P$, $^{35}S$, $^{18}F$, $^{36}Cl$, and $^{125}I$. Compounds that contain other isotopes of these and/or other atoms are within the scope of this invention.

In another embodiment, the isotope-labeled compounds contain deuterium ($^2H$), tritium ($^3H$) or $^{14}C$ isotopes. Isotope-labeled compounds of this invention can be prepared by the general methods well known to persons having ordinary skill in the art. Such isotope-labeled compounds can be conveniently prepared by carrying out the procedures disclosed in the Examples and Schemes sections by substituting a readily available isotope-labeled reagent for a non-labeled reagent. In some instances, compounds can be treated with isotope-labeled reagents to exchange a normal atom with its isotope, for example, hydrogen for deuterium can be exchanged by the action of a deuteric acid such as $D_2SO_4/D_2O$. In addition to the above, relevant procedures and intermediates are disclosed, for instance, in Lizondo, J et al., *Drugs Fut*, 21(11), 1116 (1996); Brickner, S J et al., *J Med Chem*, 39(3), 673 (1996); Mallesham, B et al., *Org Lett*, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention can be used as standards to determine the effectiveness of CB2 ligands in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., *J. Labelled Comp. Radiopharmaceut.*, 36(10):927-932 (1995); Kushner et al., *Can. J. Physiol. Pharmacol.*, 77, 79-88 (1999).

In addition, non-radio active isotope containing drugs, such as deuterated drugs called "heavy drugs," can be used for the treatment of diseases and conditions related to CB2 activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci. 1960 84: 736; Czakja D Metal., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling 0 Eds. 1994. Advanced Medical Publishing, Madison Wis. pp. 125-134; Diabetes Metab. 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one exception: because of the increased mass of the heavy isotope, any bond involving the heavy isotope and another atom can be stronger than the same bond between the light isotope and that atom. Accordingly, the incorporation of an isotope at a site of metabolism or enzymatic transformation can slow said reactions potentially altering the pharmacokinetic profile or efficacy relative to the non-isotopic compound.

c. Biological Data

In Vitro Methods—$CB_2$ and $CB_1$ Radioligand Binding Assays:

The $CB_1$ and $CB_2$ radioligand binding assays described herein are utilized to ascertain the selectivity of compounds of the present application for binding to $CB_2$ relative to CB' receptors.

HEK293 cells stably expressing human $CB_2$ receptors were grown until a confluent monolayer was formed. Briefly, the cells were harvested and homogenized in TE buffer (50 mM Tris-HCl, 1 mM $MgCl_2$, and 1 mM EDTA) using a polytron for 2×10 second bursts in the presence of protease inhibitors, followed by centrifugation at 45,000×g for 20 minutes. The final membrane pellet was re-homogenized in storage buffer (50 mM Tris-HCl, 1 mM $MgCl_2$, and 1 mM EDTA and 10% sucrose) and frozen at −78° C. until used. Saturation binding reactions were initiated by the addition of membrane preparation (protein concentration of 5 μg/well for human $CB_2$) into wells of a deep well plate containing [$^3$H] CP-55,940 (120 Ci/mmol, a nonselective CB agonist commercially available from Tocris) in assay buffer (50 mM Tris, 2.5 mM EDTA, 5 mM $MgCl_2$, and 0.5 mg/mL fatty acid free BSA, pH 7.4). After 90 min incubation at 30° C., binding reaction was terminated by the addition of 300 μL/well of cold assay buffer followed by rapid vacuum filtration through a UniFilter-96 GF/C filter plates (pre-soaked in 1 mg/mL BSA for 2 hours). The bound activity was counted in a Top-Count using Microscint-20. Saturation experiments were conducted with twelve concentrations of [$^3$H]CP-55,940 ranging from 0.01 to 8 nM. Competition experiments were conducted with 0.5 nM [$^3$H]CP-55,940 and five concentrations (0.01 nM to 10 μM) of displacing ligands. The addition of 10 μM unlabeled CP-55,940 (Tocris, Ellisville, Mo.) was used to assess nonspecific binding.

HEK293 cells stably expressing rat $CB_2$ receptors were grown until a confluent monolayer was formed. Briefly, the cells were harvested and homogenized in TE buffer (50 mM Tris-HCl, 1 mM $MgCl_2$, and 1 mM EDTA) using a polytron for 2×10 second bursts in the presence of protease inhibitors, followed by centrifugation at 45,000×g for 20 minutes. The final membrane pellet was re-homogenized in storage buffer (50 mM Tris-HCl, 1 mM $MgCl_2$, and 1 mM EDTA and 10% sucrose) and frozen at −78° C. until used. Saturation binding reactions were initiated by the addition of membrane preparation (protein concentration of 20 μg/well for rat $CB_2$) into wells of a deep well plate containing [$^3$H]CP-55,940 (120 Ci/mmol, a nonselective CB agonist commercially available from Tocris) in assay buffer (50 mM Tris, 2.5 mM EDTA, 5 mM $MgCl_2$, and 0.5 mg/mL fatty acid free BSA, pH 7.4). After 45 min incubation at 30° C., binding reaction was terminated by the addition of 300 μL/well of cold assay buffer followed by rapid vacuum filtration through a UniFilter-96 GF/C filter plates (pre-soaked in 1 mg/mL BSA for 2 hours). The bound activity was counted in a TopCount using Microscint-20. Saturation experiments were conducted with twelve concentrations of [$^3$H]CP-55,940 ranging from 0.01 to 8 nM. Competition experiments were conducted with 0.5 nM [$^3$H] CP-55,940 and five concentrations of displacing ligands selected from the range of 0.01 nM to 10 μM. The addition of 10 μM unlabeled CP-55,940 (Tocris, Ellisville, Mo.) was used to assess nonspecific binding.

Certain compounds tested bound to $CB_2$ receptors with $K_i$ of equal or less than about 1,000 nM, for example, less than 400 nM, or less than 200 nM, or less than 100 nM.

TABLE 1

| Example # | human $CB_2$ binding ($K_i$, nM) | rat $CB_2$ binding ($K_i$, nM) |
|---|---|---|
| 1 | 122.71 | 44.21 |
| 2 | 1000.00 | 459.47 |
| 3 | 46.37 | 29.09 |
| 4 | 1000.00 | 104.13 |
| 5 | 199.14 | 1000.00 |
| 6 | 1000.00 | 420.21 |

HEK293 human $CB_1$ membranes were purchased from Perkin Elmer. Binding was initiated by the addition of membranes (8-12 µg per well) into wells (Scienceware 96-well DeepWell plate, VWR, West Chester, Pa.) containing [$^3$H] CP-55,940 (120 Ci/mmol, Perkin Elmer, Boston, Mass.) and a sufficient volume of assay buffer (50 mM Tris, 2.5 mM EDTA, 5 mM $MgCl_2$, and 0.5 mg/mL fatty acid free BSA, pH 7.4) to bring the total volume to 250 µL. After incubation (30° C. for 90 minutes), binding was terminated by the addition of 300 µL per well of cold assay buffer and rapid vacuum filtration (FilterMate Cell Harvester, Perkin Elmer, Boston, Mass.) through a UniFilter-96 GF/C filter plate (Perkin Elmer, Boston, Mass.) (pre-soaked in 0.3% PEI at least 3 hours), followed by five washes with cold assay buffer. The bound activity was counted in the TopCount using Microscint-20 (both from Perkin Elmer, Boston, Mass.). Competition experiments were conducted with 1 nM [$^3$H]CP-55,940 and five concentrations (1 nM to 10 µM) of displacing ligands. The addition of 10 µM unlabeled CP-55,940 (Tocris, Ellisville, Mo.) was used to assess nonspecific binding. Certain compounds tested for $CB_1$ binding, bound to $CB_1$ receptors with $K_i$ values 10×-1000× higher than the $K_i$ for $CB_2$. These results show that the compounds of the present application preferably bind to $CB_2$ receptors, therefore are selective ligands for the $CB_2$ receptor.

d. Methods Of Using The Compounds

One embodiment provides methods for treating pain (for example, inflammatory pain, osteoarthritis pain, eye pain, lower back pain, post-operative pain, cancer pain, neuropathic pain, nociceptive pain, or combinations thereof) in mammals (including human) in need of such treatment. The methods comprise administering to the mammals therapeutically effective amounts of one or more compounds described herein, or pharmaceutically acceptable salts, solvates, or salts of solvates thereof. The methods further comprise administration of compounds described herein as a single dose. The methods also comprise repeated or chronic administration of present compounds over a period of days, weeks, months, or longer. In certain embodiments, the method comprises administering to the mammal therapeutically effective amounts of one or more of the compounds described herein, or pharmaceutically acceptable salts, solvates, or salts of solvates thereof, in combination with one or more analgesics (for example, acetaminophen or opioids such as, but not limited to, morphine, oxycodone, or related opioids), or with one or more nonsteroidal anti-inflammatory drug (NSAID); or administered with a combination of one or more analgesics and one or more NSAID. Examples of suitable NSAID include, but not limited to, aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac. In certain embodiments, the nonsteroidal anti-inflammatory drug (NSAID) is ibuprofen. In certain embodiments, the composition can optionally include one or more pharmaceutically acceptable carriers.

Another embodiment provides methods for treating disorders selected from the group consisting of inflammatory disorders, immune disorders, neurological disorders, cancers of the immune system, respiratory disorders, and cardiovascular disorders in mammals (including human) in need of such treatment. The methods comprise administering to the mammal therapeutically effective amounts of one or more compounds described herein or pharmaceutically acceptable salts, solvates, or salts of solvates thereof, optionally in the presence of one or more pharmaceutically acceptable carriers.

Yet another embodiment relates to methods for providing neuroprotection in mammals (including human) in need of such treatment. These methods comprise administering to the mammal therapeutically effective amounts of one or more compounds described herein or pharmaceutically acceptable salts, solvates, or salts of solvates thereof, optionally in the presence of one or more pharmaceutically acceptable carriers.

Another embodiment of the present invention provides a method of increasing the therapeutic effectiveness or potency of compounds of the invention by repeated or chronic administration over a period of days, weeks, or months.

In addition to the data contained herein, several lines of evidence support the assertion that $CB_2$ receptors play a role in analgesia. HU-308 is one of the first highly selective $CB_2$ agonists identified that elicits an antinociceptive response in the rat formalin model of persistent pain (Hanus, L., et al., Proc. Nat. Acad. Sci., 1999, 96, 14228-14233). The $CB_2$-selective cannabinoid ligand AM-1241 exhibits robust analgesic efficacy in animal models of acute thermal pain (Malan, T. P., et al., Pain, 2001, 93, 239-245; Ibrahim, M. M., et al., Proc. Nat. Acad. Sci., 2005, 102(8), 3093-3098), persistent pain (Hohmann, A. G., et al., J. Pharmacol. Exp. Ther., 2004, 308, 446-453), inflammatory pain (Nackley, A. G., et al., Neuroscience, 2003, 119, 747-757; Quartilho, A. et al., Anesthesiology, 2003, 99, 955-60), and neuropathic pain (Ibrahim, M. M., et al., Proc. Nat. Acad. Sci., 2003, 100, 10529-10533). The $CB_2$-selective partial agonist GW405833, also known as L768242, is efficacious in rodent models of neuropathic, incisional, and both chronic and acute inflammatory pain (Valenzano, K. J., et al., Neuropharmacology, 2005, 48, 658-672 and Clayton, N., et al., Pain, 2002, 96, 253-260).

The potential exists for $CB_2$ modulators to have opioid sparing effects. A synergy between the analgesic effects of morphine and the nonselective CB agonist $\Delta^9$-THC has been documented (Cichewicz, D. L., Life Sci. 2004, 74, 1317-1324). Therefore, $CB_2$ ligands have additive or synergistic analgesic effects when used in combination with lower doses of morphine or other opioids, providing a strategy for reducing adverse opioid events, such as tolerance, constipation, and respiratory depression, without sacrificing analgesic efficacy.

$CB_2$ receptors are present in tissues and cell types associated with immune functions and $CB_2$ receptor mRNA is expressed by human B cells, natural killer cells, monocytes, neutrophils, and T cells (Galiegue et al., Eur. J. Biochem., 1995, 232, 54-61). Studies with $CB_2$ knockout mice have suggested a role for $CB_2$ receptors in modulating the immune system (Buckley, N. E., et al., Eur. J. Pharmacol. 2000, 396, 141-149). Although immune cell development and differentiation are similar in knockout and wild type animals, the immunosuppressive effects of $\Delta^9$-THC are absent in the $CB_2$ receptor knockout mice, providing evidence for the involvement of $CB_2$ receptors in immunomodulation. As such, selective $CB_2$ modulators can be useful for the treatment of autoimmune diseases including, but not limited to, multiple sclerosis, rheumatoid arthritis, systemic lupus, myasthenia gravis, type I diabetes, irritable bowel syndrome, psoriasis, psoriatic arthritis, and hepatitis; and immune related disorders including, but not limited to, tissue rejection in organ transplants, gluten-sensitive enteropathy (Celiac disease), asthma, chronic obstructive pulmonary disease, emphysema, bronchitis, acute respiratory distress syndrome, allergies, allergic rhinitis, dermatitis, and Sjogren's syndrome.

Microglial cells are considered to be the immune cells of the central nervous system (CNS) where they regulate the initiation and progression of immune responses. $CB_2$ receptor expression on microglia is dependent upon inflammatory state with higher levels of $CB_2$ found in primed, proliferating, and migrating microglia relative to resting or fully activated microglial (Carlisle, S. J., et al. Int. Immunopharmacol., 2002, 2, 69). Neuroinflammation induces many changes in microglia cell morphology and there is an upregulation of $CB_2$ receptors and other components of the endocannabinoid system. Neuroinflammation occurs in several neurodegenerative diseases, and induction of microglial $CB_2$ receptors has been observed (Carrier, E. J., et al., Current Drug Targets—CNS & Neurological Disorders, 2005, 4, 657-665). Thus, $CB_2$ ligands can be clinically useful for the treatment of neuroinflammation.

Multiple sclerosis is common immune-mediated disease of the CNS in which the ability of neurons to conduct impulses becomes impaired through demyelination and axonal damage. The demyelination occurs as a consequence of chronic inflammation and ultimately leads to a broad range of clinical symptoms that fluctuate unpredictably and generally worsen with age. These include painful muscle spasms, tremor, ataxia, motor weakness, sphincter dysfunction, and difficulty speaking (Pertwee, R. G., Pharmacol. Ther. 2002, 95, 165-174). The $CB_2$ receptor is up-regulated on activated microglial cells during experimental autoimmune encephalomyelitis (EAE) (Maresz, K., et al., J. Neurochem. 2005, 95, 437-445). $CB_2$ receptor activation prevents the recruitment of inflammatory cells such as leukocytes into the CNS (Ni, X., et al., Multiple Sclerosis, 2004, 10, 158-164) and plays a protective role in experimental, progressive demyelination (Arevalo-Martin, A.; et al., J. Neurosci., 2003, 23(7), 2511-2516), which are critical features in the development of multiple sclerosis. Thus, $CB_2$ receptor modulators can provide a unique treatment for demyelinating pathologies.

Alzheimer's disease is a chronic neurodegenerative disorder accounting for the most common form of elderly dementia. Recent studies have revealed that $CB_2$ receptor expression is upregulated in neurotic plaque-associated microglia from brains of Alzheimer's disease patients (Benito, C., et al., J. Neurosci., 2003, 23(35), 11136-11141). In vitro, treatment with the $CB_2$ agonist JWH-133 abrogated β-amyloid-induced microglial activation and neurotoxicity, effects that can be blocked by the $CB_2$ antagonist SR144528 (Ramirez, B. G., et al., J. Neurosci. 2005, 25(8), 1904-1913). $CB_2$ modulators can possess both anti-inflammatory and neuroprotective actions and thus have clinical utility in treating neuroinflammation and in providing neuroprotection associated with the development of Alzheimer's disease.

Increased levels of epithelial $CB_2$ receptor expression are observed in human inflammatory bowel disease tissue (Wright, K., et al., Gastroenterology, 2005, 129, 437-453). Activation of $CB_2$ receptors re-established normal gastrointestinal transit after endotoxic inflammation was induced in rats (Mathison, R., et al., Br. J. Pharmacol. 2004, 142, 1247-1254). $CB_2$ receptor activation in a human colonic epithelial cell line inhibited TNF-α-induced interleukin-8 (IL-8) release (Ihenetu, K. et al., Eur. J. Pharmacol. 2003, 458, 207-215). Chemokines released from the epithelium, such as the neutrophil chemoattractant IL-8, are upregulated in inflammatory bowel disease (Warhurst, A. C., et al., Gut, 1998, 42, 208-213). Thus, administration of $CB_2$ receptor modulators can represent a novel approach for the treatment of inflammation and disorders of the gastrointestinal tract including but not limited to inflammatory bowel disease, irritable bowel syndrome, secretory diarrhea, ulcerative colitis, Crohn's disease and gastroesophageal reflux disease (GERD).

Hepatic fibrosis occurs as a response to chronic liver injury and ultimately leads to cirrhosis, which is a major worldwide health issue due to the severe accompanying complications of portal hypertension, liver failure, and hepatocellular carcinoma (Lotersztajn, S., et al., Annu Rev. Pharmacol. Toxicol., 2005, 45, 605-628). Although $CB_2$ receptors were not detectable in normal human liver, $CB_2$ receptors were expressed liver biopsy specimens from patients with cirrhosis. Activation of $CB_2$ receptors in cultured hepatic myofibroblasts produced potent antifibrogenic effects (Julien, B., et al., Gastroenterology, 2005, 128, 742-755). In addition, $CB_2$ knockout mice developed enhanced liver fibrosis after chronic administration of carbon tetrachloride relative to wild-type mice. Administration of $CB_2$ receptor modulators can represent a unique approach for the treatment of liver fibrosis.

Cough is a dominant and persistent symptom of many inflammatory lung diseases, including asthma, chronic obstructive pulmonary disease, viral infections, and pulmonary fibrosis (Patel, H. J., et al., Brit. J. Pharmacol., 2003, 140, 261-268). Recent studies have provided evidence for the existence of neuronal $CB_2$ receptors in the airways, and have demonstrated a role for $CB_2$ receptor activation in cough suppression (Patel, H. J., et al., Brit. J. Pharmacol., 2003, 140, 261-268 and Yoshihara, S., et al., Am. J. Respir. Crit. Care Med., 2004, 170, 941-946). Both exogenous and endogenous cannabinoid ligands inhibit the activation of C-fibers via $CB_2$ receptors and reduce neurogenic inflammatory reactions in airway tissues (Yoshihara, S., et al., J. Pharmacol. Sci. 2005, 98(1), 77-82; Yoshihara, S., et al., Allergy and Immunology, 2005, 138, 80-87). Thus, $CB_2$-selective modulators can have utility as antitussive agents for the treatment of pulmonary inflammation, chronic cough, and a variety of airway inflammatory diseases including but not limited to asthma, chronic obstructive pulmonary disease, and pulmonary fibrosis.

There is a substantial genetic contribution to bone mass density and the $CB_2$ receptor gene is associated with human osteoporosis (Karsak, M., et al., Human Molecular Genetics, 2005, 14(22), 3389-3396). Osteoclasts and osteoblasts are largely responsible for maintaining bone structure and function through a process called remodeling, which involves resorption and synthesis of bone (Boyle, W. J., et al., Nature, 2003, 423, 337-342). $CB_2$ receptor expression has been detected on osteoclasts and osteoblastic precursor cells, and administration of a $CB_2$ agonist in mice caused a dose-dependent increase in bone formation (Grotenhermen, F. and Muller-Vahl, K., Expert Opin. Pharmacother., 2003, 4(12), 2367-2371). Cannabinoid inverse agonists, including the $CB_2$-selective inverse agonist SR144528, have been shown to inhibit osteoclast activity and reverse ovariectomy-induced bone loss in mice, which is a model for post-menopausal osteoporosis (Ralston, S. H., et al., Nature Medicine, 2005, 11, 774-779). Thus, $CB_2$ modulators can be useful for the treatment and prevention of osteoporosis, osteoarthritis, and bone disorders.

Arthrosclerosis is a chronic inflammatory disease and is a leading cause of heart disease and stroke. $CB_2$ receptors have been detected in both human and mouse atherosclerotic plaques. Administration of low doses of THC in apolipoprotein E knockout mice slowed the progression of atherosclerotic lesions, and these effects were inhibited by the $CB_2$-selective antagonist SR144528 (Steffens, S., et al., Nature, 2005, 434, 782-786). Thus, compounds with activity at the $CB_2$ receptor can be clinically useful for the treatment of atherosclerosis.

$CB_2$ receptors are expressed on malignant cells of the immune system and targeting $CB_2$ receptors to induce apoptosis can constitute a novel approach to treating malignancies of the immune system. Selective $CB_2$ agonists induce regression of malignant gliomas (Sanchez, C., et al., Cancer Res., 2001, 61, 5784-5789), skin carcinomas (Casanova, M. L., et al., J. Clin. Invest., 2003, 111, 43-50), and lymphomas (McKallip, R. J., et al., Blood, 2002, 15(2), 637-634). Thus, $CB_2$ modulators can have utility as anticancer agents against tumors of immune origin.

Activation of $CB_2$ receptors has been demonstrated to protect the heart against the deleterious effects of ischemia and reperfusion (Lepicier, P., et al., Brit. J. Pharm. 2003, 139, 805-815; Bouchard, J.-F., et al., Life Sci. 2003, 72, 1859-1870; Filippo, C. D., et al., J. Leukoc. Biol. 2004, 75, 453-459). Thus, $CB_2$ modulators can have utility for the treatment or prophylaxis of cardiovascular disease and the development of myocardial infarction.

Actual dosage levels of active ingredients in the pharmaceutical compositions can be varied so as to obtain an amount of the active compound(s) that is effective to achieve the desired therapeutic response for a particular patient, compositions and mode of administration. The selected dosage level can depend upon the activity of the particular compound, the route of administration, the duration of treatment, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved. In the treatment of certain medical conditions, repeated or chronic administration of the active ingredients can be required to achieve the desired therapeutic response. "Repeated or chronic administration" refers to the administration of the compositions described herein daily (i.e., every day) or intermittently (i.e., not every day) over a period of days, weeks, months, or longer. In particular, the treatment of chronic painful conditions is anticipated to require such repeated or chronic administration of the compositions described herein. Compounds of the invention can become more effective upon repeated or chronic administration such that the therapeutically effective doses on repeated or chronic administration can be lower than the therapeutically effective dose from a single administration.

Compounds can also be administered as a pharmaceutical composition comprising the compounds of interest in combination with one or more pharmaceutically acceptable carriers. The phrase "therapeutically effective amount" of the present compound means a sufficient amount of the compound to treat disorders, at a reasonable benefit/risk ratio applicable to any medical treatment. It can be understood, however, that the total daily usage of the compounds and compositions can be decided by the attending physician within the scope of sound medical judgment. The specific therapeutically effective dose level for any particular patient can depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

Compounds can be administered alone, or in combination (i.e. co-administered) with one or more additional pharmaceutical agents. For example, one or more present compounds or pharmaceutically acceptable salts, solvates, or salts of solvates thereof, can be administered in combination with one or more analgesics (e.g acetaminophen or opioids), or with one or more nonsteroidal anti-inflammatory drug (NSAID), or mixtures thereof. Non limiting examples of suitable NSAID include aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac. In certain embodiments, the nonsteroidal anti-inflammatory drug (NSAID) is ibuprofen. Combination therapy includes administration of a single pharmaceutical dosage formulation containing one or more of the compounds and one or more additional pharmaceutical agents, as well as administration of the compounds and each additional pharmaceutical agent in its own separate pharmaceutical dosage formulation. For example, one or more active ingredients (including present compounds and additional pharmaceutical agents) can be administered to the patient together, in a single oral dosage composition having a fixed ratio of each active ingredient, such as a tablet or capsule; or each active ingredient can be administered in separate oral dosage formulations.

Separate dosage formulations can be administered at essentially the same time (e.g., concurrently) or at separately staggered times (e.g., sequentially).

Therapeutically effective amounts can be determined by those skilled in the art, and can be adjusted to the requirements of each particular case. Generally, a therapeutically effective amount of a $CB_2$ modulator can range from a total daily dose, for example in human or other animals, of about 0.01 mg/kg body weight to about 100 mg/kg body weight, preferably of about 0.03 mg/kg body weight to about 30 mg/kg body weight. If desired, the effective daily dose can be divided into multiple doses for purposes of administration. Consequently, single dose compositions can contain such amounts or submultiples thereof to make up the daily dose. It is understood that the effective daily dose can vary with the duration of the treatment.

e. Pharmaceutical Compositions

Pharmaceutical compositions comprising compounds described herein or pharmaceutically acceptable salts, solvates, or salts of solvates thereof are also provided. The pharmaceutical compositions comprise compounds of interest formulated together with one or more non-toxic pharmaceutically acceptable carriers.

Another aspect relates to pharmaceutical compositions comprising compounds described herein, or pharmaceutically acceptable salts, solvates, or salts of solvates thereof, and one or more pharmaceutically acceptable carriers, alone or in combination with one or more analgesics (e.g. acetaminophen or opioids such as, but not limited to, morphine, oxycodone, or related opioids), or in combination with one or more nonsteroidal anti-inflammatory drug (NSAID), or a combination of one or more analgesics and one or more NSAID.

The pharmaceutical compositions can be administered to humans and other mammals orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions for parenteral injection comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions can also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It can also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound can be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form can also comprise buffering agents.

Solid compositions of a similar type can also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They can optionally contain opacifying agents and can also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions can also include adjuvants such as wetting agents, emulsifying and suspending agents, sweetening, flavoring and perfuming agents.

Suspensions, in addition to the active compounds, can contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Present compounds can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration include powders, sprays, ointments and inhalants. The active compound can be mixed under sterile conditions with a pharmaceutically acceptable carrier and any needed preservatives, buffers or propellants which can be required. Ophthalmic formulations, eye ointments, powders and solutions are also contemplated as being within the scope of this invention.

Compounds described herein can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use.

Contemplated also are compounds formed by synthetic means or formed by in vivo biotransformation of a prodrug.

Compounds described herein can exist in unsolvated as well as solvated forms, including hydrated forms, such as hemi-hydrates. In general, the solvated forms, with pharmaceutically acceptable solvents such as water and ethanol among others are equivalent to the unsolvated forms.

f. General Synthesis

This invention is intended to encompass compounds when prepared by synthetic processes or by metabolic processes. Preparation of the compounds by metabolic processes includes those occurring in the human or animal body (in vivo) or processes occurring in vitro.

The compounds can be prepared by a variety of processes well known for the preparation of compounds of this class. For example, the compounds wherein the groups A, $X^1$, $X^2$, $R^1$, $R^{1a}$, $R^{1b}$, $R^3$, $R^4$, $R^5$, $R^{10}$, $R^{11}$, $R^{12}$, $R^{21}$, $R^{22}$, $R^{24}$, $G^1$, $R^{1m}$, $R^x$, $R^y$, q1, and z have the meanings as set forth in the summary section unless otherwise noted, can be synthesized as shown in Schemes 1-5.

Abbreviations which have been used in the descriptions of the Schemes and the Examples that follow are: DMF for N,N-dimethylformamide, DMSO for dimethyl sulfoxide, $Et_2O$ for diethyl ether, EtOAc for ethyl acetate, $Et_3N$ for triethylamine, MeOH for methanol, THF for tetrahydrofuran, OTs for tosylate, OMs for mesylate, and THF for tetrahydrofuran.

Scheme 1

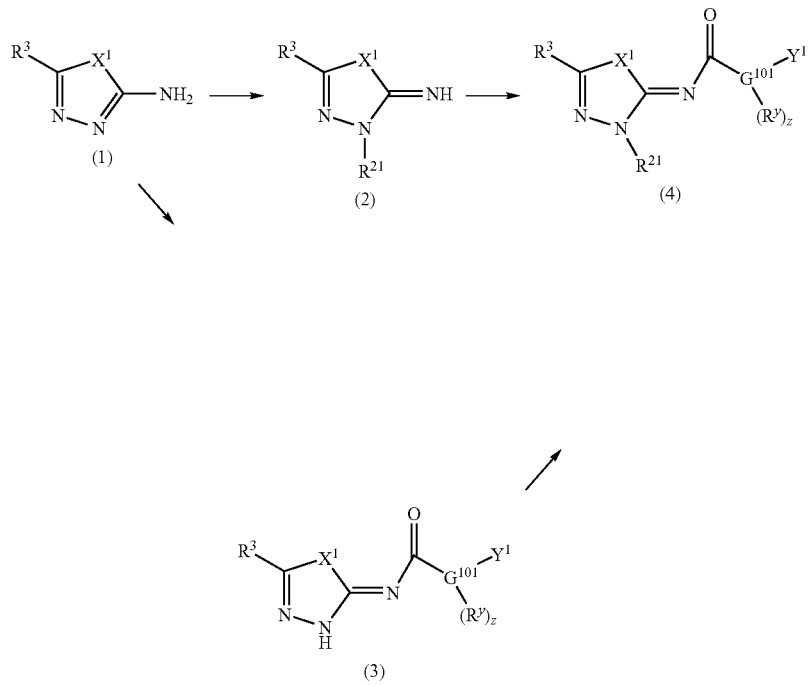

Compounds of formula (4) wherein $G^{101}$ is aryl, heteroaryl, heterocycle, cycloalkyl, or cycloalkenyl, and $Y^1$ is F, —O-$G^1$, or —O—$(CR^{1a}R^{1b})_{q1}$—$(N(R^{1m}))_2$ can be prepared according to the methods illustrated in Scheme 1. Heteroaryl amines of formula (1) can be first reacted with compounds of formula $R^{21}$—$X^{101}$, wherein $X^{101}$ is Cl, Br, I, OTs, or OMs, to form the intermediate (2). This reaction can be performed either neat or in a solvent such as, but not limited to, tetrahydrofuran, acetonitrile, dimethylformamide, dimethylsulfoxide, or dioxane, at about room temperature to about 150° C., and optionally in the presence of a catalyst such as but not limited to tetrabutylammonium iodide or sodium iodide. In certain cases, it can be beneficial to conduct this reaction in the presence of a base such as, but not limited to, triethylamine, potassium carbonate, potassium tert-butoxide, or sodium hydride. The intermediate (2) can be converted to the products (4) by reaction with an appropriate acid chloride or carboxylic acid. For example, intermediate (2) can be reacted with an acid chloride in a solvent such as, but not limited to, tetrahydrofuran, dimethylformamide, or dichloromethane at a temperature from about 25° C. to about 50° C. in the presence of a base such as, but not limited to, triethylamine, diisopropylethylamine, or potassium carbonate, and optionally in the presence of a catalyst such as 4-dimethylaminopyridine. Alternatively, intermediate (2) can be reacted with a carboxylic acid in a solvent such as, but not limited to, tetrahydrofuran or dimethylformamide in the presence of a coupling reagent such as 1,1'-carbonyldiimidazole (CDI), bis(2-oxo-3-oxazolidinyl)phosphinic chloride (BOPCl), 1,3-dicyclohexylcarbodiimide (DCC), polymer supported 1,3-dicyclohexylcarbodiimide (PS-DCC), O-(7-azabenzotriazol-1-yl)-N,N,N',N'-tetramethyluronium hexafluorophosphate (HATU), O-benzotriazol-1-yl-N,N,N',N'-tetramethyluronium tetrafluoroborate (TBTU), or 1-propanephosphonic acid cyclic anhydride, in the presence or absence of a coupling auxiliary such as, but not limited to, or 1-hydroxy-7-azabenzotriazole (HOAT) or 1-hydroxybenzotriazole hydrate (HOBT). The reaction is generally conducted in the presence or absence of a base such as, but not limited to, N-methyl morpholine, triethylamine, or diisopropylethylamine.

Compounds (1) can also be converted to intermediates (3) by reaction with an acid chloride or carboxylic acid using reaction conditions as described for the conversion of (2) to (4). The intermediate (3) can then be converted to (4) by reaction with $R^{21}$—$X^{101}$, wherein $X^{101}$ is Cl, Br, I, OTs, or OMs, using reaction conditions as described for the transformation of (1) to (2).

Similarly, other compounds of general formula (I) wherein Ring A represents formulae (b)-(d) can be prepared from the appropriate heteroaryl or heterocyclic amines using procedures analogous to Scheme 1.

The heteroaryl amines can be obtained from commercial sources or can be prepared using methods well-known to those skilled in the art. For example, heteroaryl amines of formula (1) wherein $X^1$ is sulfur can be prepared using general procedures as illustrated in Scheme 2.

Scheme 2

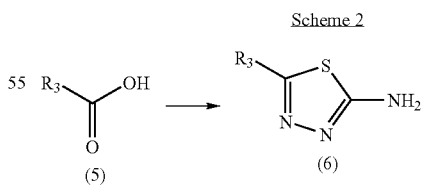

Carboxylic acids of formula (5) can be treated with thiosemicarbazide and phosphorus oxychloride at a temperature of about 90° C., in a solvent such as, but not limited to, dioxane to provide compounds of formula (6).

Compounds of general formula (I) wherein ring A is formula (b) and $X^2$ is $N(R^{10})$ can be synthesized, for example, using the general procedures as outlined in Scheme 3.

Scheme 3

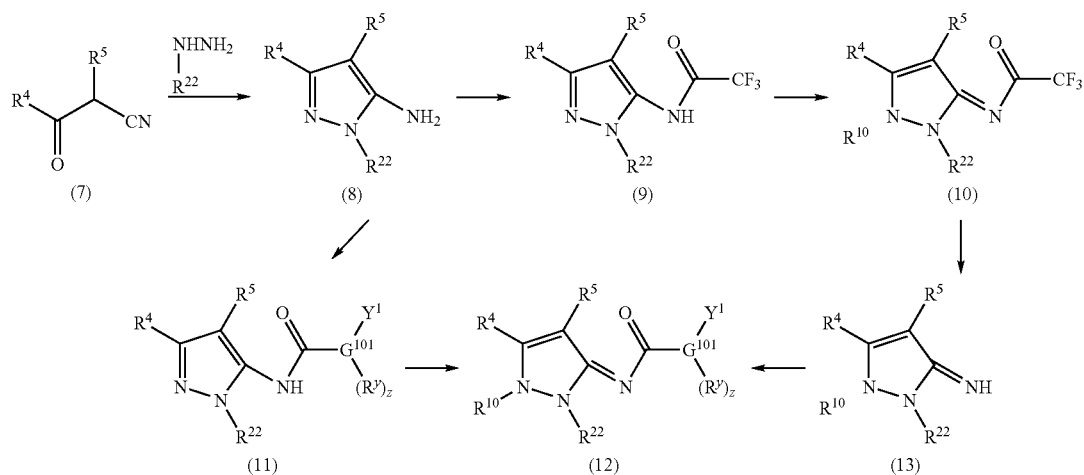

Hydrazines of formula $R^{22}$—$NHNH_2$ can be reacted with ketonitriles (7) in a solvent such as, but not limited to, ethanol, at a temperature of between about 0° C. to about 80° C., to provide intermediates of formula (8). These intermediate aminopyrazoles (8) can be treated with appropriate carboxylic acids or acid chlorides according to the methods outlined in Scheme 1 for the conversion of (2) to (4) to provide pyrazoles (7). Compounds (11) wherein $G^{101}$ and $Y^1$ are as defined above can be converted to (12) by reaction with an appropriate alkylating agent such as, but not limited to, a halide, mesylate, tosylate, triflate, sulfate, or diphenylmethylsulfonium tetrafluoroborate, either neat or in a solvent such as, but not limited to, tetrahydrofuran, toluene, acetonitrile, or dioxane. This reaction can be conducted from about 0° C. to about 150° C. In certain cases the addition of a base can be beneficial. Examples of bases that can be used include triethylamine, diisopropylethylamine, potassium carbonate, sodium hydride, sodium hydroxide, and lithium diisopropylamide.

Alternatively, compounds of formula (8) can be converted to the trifluoroacetamide (9) by reaction with trifluoroacetic anhydride in a solvent such as, but not limited to, methylene chloride and in the presence of a base such as, but not limited to, pyridine or triethylamine. Compounds (9) can be converted to compounds (10) using the conditions described above for the conversion of (11) to (12). Compounds of formula (10) can be converted to (13) by reaction with aqueous potassium or sodium hydroxide with methanol or ethanol as a co-solvent at temperatures from about room temperature to about 70° C. Compounds (13) can be converted to (12) by reaction with the appropriate carboxylic acid or acid chloride according to the conditions of Scheme 1 for the conversion of (2) to (4).

Alternatively, intermediates of formula (8) can be synthesized utilizing general procedures as illustrated in Scheme 4.

Scheme 4

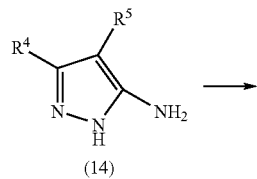

-continued

[Structures (15), (16), (8)]

Aminopyrazoles (14) can be converted to the amidine intermediates (15) by refluxing in dimethylformamide dimethylacetal or refluxing with a 2- to 3-fold excess of dimethylformamide dimethylacetal in dioxane or other aprotic solvent. Compounds (15), in turn, can be alkylated with reagents $R^{22}$—$X^{202}$ wherein $X^{202}$ halide, OTs, OMs, or triflate, under phase transfer conditions, for example, by conducting the reaction in a toluene/water mixture with a phase transfer reagent like tetrabutylammonium hydrogensulfate or tetrabutylammonium iodide at a temperature from about 50° C. to about 110° C., with potassium carbonate as base to provide the intermediates (16). The intermediates (16) can be converted to the intermediates (8) by reaction with hydrazine hydrate in the presence of acetic acid in a solvent such as, but not limited to, dioxane at temperatures from about 50-100° C. The foregoing sequence to install the $R^{22}$ group can also be accomplished by using a triphenylmethyl(trityl) group on the exocyclic nitrogen of (14) instead of the amidine. Typical conditions for effecting the analogous alkylation in the presence of a trityl group include, but are not limited to, reaction with an alkylating agent $R^{22}$—$X^{202}$ in the presence of a base such as sodium hydride or potassium tert-butoxide in a solvent such as dimethylformamide or tetrahydrofuran. The trityl protecting group can be removed using methods well-known to those skilled in the art such as, for example, treatment of the compound with an acid such as, but not limited to, hydrochloric acid.

Compounds of formula (I) wherein ring A is formula (d) can be prepared by the general procedure as shown Scheme 5.

Scheme 5

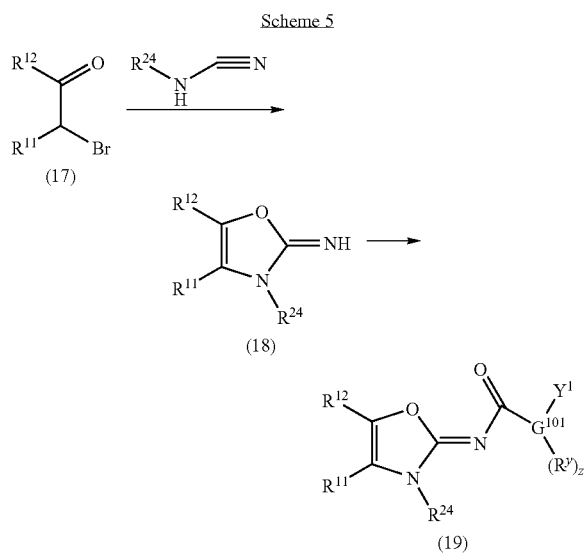

Compounds of formula (17) when treated with compounds of formula $R^{24}N\!=\!CN$ in the presence of potassium carbonate, sodium carbonate, or cesium carbonate and in a solvent such as, but not limited to, tetrahydrofuran, dimethoxyethane, dioxane, or methyl ethyl ketone, at a temperature from about 25° C. to about 100° C. are transformed to intermediates of formula (18). Intermediates of formula (18) can be converted to compounds of formula (19) wherein $G^{101}$ and $Y^1$ are as defined above by reaction with an acid chloride or carboxylic acid using reaction conditions as described in Scheme 1.

Compounds of formula (I) wherein A is (b) and $X^2$ is O, and compounds of formula (I) wherein ring A is formula (c) can be prepared from isoxazole-3-amines and pyridine-2-amines using synthetic methods that are analogous to those in Schemes 1. The starting isoxazole-3-amines and pyridine-2-amines are either commercially available or can be prepared by known synthetic methods described in the chemical literature.

In the above illustrated synthetic schemes, compounds having $Y^1$ is F can be converted to those wherein $Y^1$ is —O-$G^1$ or —O—$(CR^{1a}R^{1b})_{q1}$—$(N(R^{1m})_2$ by treatment, for example, with the appropriate alcohols in the presence of a base such as, but not limited to, triethylamine, potassium tert-butoxide, sodium tert-butoxide or sodium hydride in a solvent such as, but not limited to, tetrahydrofuran or dimethylformamide at temperatures from 0° C. to 150° C. This reaction can be assisted by microwave irradiation.

It can be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step can vary depending on the particular reactants employed and substituents present in the reactants used. Unless otherwise specified, solvents, temperatures and other reaction conditions can be readily selected by one of ordinary skill in the art. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature.

Routine experimentations, including appropriate manipulation of the reaction conditions, reagents and sequence of the synthetic route, protection of any chemical functionality that can not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in T. Greene and P. G. M. Wuts, Protecting Groups in Organic Synthesis ($3^{rd}$ ed.), John Wiley & Sons, NY (1999), which is incorporated herein by reference in its entirety. Synthesis of the compounds of the invention can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it can be obtained by carrying out one of the above procedures using a pure geometric isomer as a starting material, or by resolution of a mixture of the geometric isomers of the compound or intermediates using a standard procedure such as chromatographic separation.

The following examples are for illustrative purposes and should not be deemed to narrow the scope of the invention.

g. EXAMPLES

Example 1

2-[2-(tert-butylamino)ethoxy]-N-[(3E)-5-tert-butyl-2-(cyclopropylmethyl)-1-methyl-1,2-dihydro-3H-pyrazol-3-ylidene]-5-(trifluoromethyl)benzamide Example 1A di-tert-butyl 1-(cyclopropylmethyl)hydrazine-1,2-dicarboxylate To a mixture of cyclopropylmethanol (10.1 g, 140 mmol), di-tert-butyl hydrazine-1,2-dicarboxylate (6.50 g, 28.0 mmol) and triphenylphosphine (44.1 g, 168 mmol) in tetrahydrofuran (100 mL) was added di-tert-butyl azodicarboxylate (38.7 g, 168 mmol) in portions. The mixture was stirred at room temperature for 3 hours then diluted with water and ethyl acetate. The organic extract was washed with brine, dried (MgSO$_4$), filtered, and concentrated. The residue was purified by column chromatography using an Analogix® Intelliflash280™ (SiO$_2$, eluted with a gradient of 0-100% hexanes in ethyl acetate) to provide the title compound (39 g, 97% yield). $^1$H NMR (300 MHz, CDCl$_3$) δ ppm 0.16-0.27 (m, 2 H), 0.40-0.54 (m, 2 H), 0.94-1.09 (m, 1 H), 1.47 (s, 9 H), 1.48 (s, 9 H), 3.31 (d, J=6.10 Hz, 2 H), 6.38 (s, 1 H).

Example 1B (cyclopropylmethyl)hydrazine dihydrochloride

A solution of Example 1A (18.0 g, 62.9 mmol) and HCl in dioxane (4 N, 100 mL) was stirred at room temperature overnight. The resulting white solid was filtered, washed with ether (20 mL), and dried to provide the title compound (9.50 g, 59.7 mmol, 95% yield), which was used in the next step. $^1$H NMR (300 MHz, DMSO-d$_6$) δ ppm 0.22-0.34 (m, 2 H), 0.46-0.58 (m, 2 H), 0.91-1.06 (m, 1 H), 2.79 (d, J=7.12 Hz, 2 H), 5.91 (s, 5 H); MS (DCI) m/z 87 [M+H]$^+$.

Example 1C 3-tert-butyl-1-(cyclopropylmethyl)-1H-pyrazol-5-amine hydrochloride

A mixture of Example 1B (13.5 g, 85 mmol) and 4,4-dimethyl-3-oxopentanenitrile (11.7 g, 93 mmol) in ethanol (100 mL) was heated at reflux for 6 hours. The mixture was cooled to room temperature, and concentrated under reduced pressure. The residue was diluted with ethyl acetate (20 mL). The resulting white precipitate was filtered, washed with ether, and dried to yield 17.5 g (90%) of title compound. $^1$H NMR (300 MHz, DMSO-d$_6$) δ ppm 0.42-0.54 (m, 4 H), 1.16-1.27 (m, 1 H), 1.28 (s, 9 H), 4.38 (d, J=7.12 Hz, 2 H), 4.80 (br, 2 H), 5.53 (s, 1 H), 15.5 (br, 1 H); MS (DCI) m/z 194 [M+H]$^+$.

Example 1D

N-(3-tert-butyl-1-(cyclopropylmethyl)-1H-pyrazol-5-yl)-2,2,2-trifluoroacetamide

To a mixture of Example 1C (13 g, 56.6 mmol) and pyridine (18.3 mL, 226 mmol) in dichloroethane (150 mL) was added 2,2,2-trifluoroacetic anhydride (15.73 mL, 113 mmol) dropwise at ambient temperature. The mixture was stirred at ambient temperature for 2 hours, and then water (20 mL) and dichloromethane (20 mL) were added. The organic layer was washed with saturated sodium bicarbonate and brine, and concentrated. The residue was purified by column chromatography using an Analogix® Intelliflash280™ (SiO$_2$, eluted with a gradient of 0-40% hexanes in ethyl acetate) to afford the title compound (14.4 g, 88%). $^1$H NMR (300 MHz, DMSO-d$_6$) δ ppm 0.21-0.33 (m, 2 H), 0.38-0.49 (m, 2 H), 1.04-1.16 (m, 1 H), 1.23 (s, 9 H), 3.82 (d, J=6.78 Hz, 2 H), 6.17 (s, 1 H), 11.31 (s, 1 H); MS (ESI) m/z 290 [M+H]$^+$.

Example 1E (E)-N-(5-tert-butyl-2-(cyclopropylmethyl)-1-methyl-1H-pyrazol-3(2H)-ylidene)-2,2,2-trifluoroacetamide A mixture of Example 1D (11.6 g, 40 mmol) and dimethyl sulfate (20.2 g, 160 mmol) in toluene (10 mL) was heated at 80° C. for 24 hours. The mixture was cooled to room temperature and concentrated. The residue was purified by column chromatography using an Analogix® Intelliflash280™ (SiO$_2$, eluted with a gradient of 15-100% hexane in solvent B, solvent B: 10:1:0.5 ethyl acetate:methanol:triethylamine) to afford the title compound (8.7 g, 72% yield). $^1$H NMR (300 MHz, DMSO-d$_6$) δ ppm 0.41-0.53 (m, 4 H), 1.15-1.27 (m, 1 H), 1.38 (s, 9 H), 3.98 (s, 3 H), 4.20 (d, J=7.12 Hz, 2 H), 6.70 (s, 1 H); MS (ESI) m/z 304 [M+H]$^+$.

Example 1F 5-tert-butyl-2-(cyclopropylmethyl)-1-methyl-1H-pyrazol-3(2H)-imine

A mixture of 1E (8.7 g, 28.8 mmol) and sodium hydroxide solution (6N, 20 mL) in methanol (100 mL) was stirred at 50° C. overnight, cooled to room temperature, and concentrated under reduced pressure. The residue was extracted with CH$_2$Cl$_2$ (3×100 mL) and the combined organic layers were washed with brine, dried (MgSO$_4$), filtered, and concentrated to afford the title compound (5.3 g, 89% yield) as white solid. $^1$H NMR (300 MHz, DMSO-d$_6$) δ ppm 0.37-0.44 (m, 2 H), 0.47-0.54 (m, 2 H), 1.07-1.20 (m, 1 H), 1.29-1.36 (m, 9 H), 3.78 (s, 3 H), 4.10 (d, J=6.74 Hz, 2 H), 5.60 (s, 1 H), 7.19 (s, 1 H); MS (+DCI) m/z 208 [M+H]$^+$.

Example 1G (E)-N-(5-tert-butyl-2-(cyclopropylmethyl)-1-methyl-1H-pyrazol-3(2H)-ylidene)-2-fluoro-5-(trifluoromethyl)benzamide To Example 1F (3.52 g, 17 mmol) in CH$_2$Cl$_2$ (50 mL) was added triethylamine (7.1 mL, 51 mmol), followed by addition of 2-fluoro-5-(trifluoromethyl)benzoyl chloride (3.85 g, 17 mmol) dropwise. The mixture was stirred at ambient temperature for 2 hours. Water (20 mL) and CH$_2$Cl$_2$ (20 mL) were added. The organic layer was separated, washed with brine, and concentrated. The residue was purified by column chromatography using an Analogix® Intelliflash280™ (SiO$_2$, eluted with a gradient of 15-100% hexanes in solvent B, solvent B: 10:1:0.5 ethyl acetate:methanol:triethylamine) to afford the title compound (6.3 g, 93%). $^1$H NMR (300 MHz, DMSO-d$_6$) δ ppm 0.42-0.56 (m, 4 H), 1.15-1.29 (m, 1 H), 1.40 (s, 9 H), 3.95 (s, 3 H), 4.24 (d, J=7.14 Hz, 2 H), 6.84 (s, 1 H), 7.33-7.43 (m, 1 H), 7.70-7.78 (m, 1H), 8.12 (dd, J=6.74, 2.38 Hz, 1 H); MS (DCI) m/z 398 [M+H]$^+$.

Example 1H

2-[2-(tert-butylamino)ethoxy]-N-[(3E)-5-tert-butyl-2-(cyclopropylmethyl)-1-methyl-1,2-dihydro-3H-pyrazol-3-ylidene]-5-(trifluoromethyl)benzamide To a solution of 2-(tert-butylamino)ethanol (118 mg, 1.007 mmol) in THF (6 mL) was added potassium 2-methylpropan-2-olate (113 mg, 1.007 mmol). The mixture was stirred at ambient temperature for 20 minutes before example 1G (200 mg, 0.503 mmol) was added in one portion. The mixture was stirred at ambient temperature for 2 hours, quenched with saturated aqueous NaHCO$_3$ (10 mL), and diluted with EtOAc (15 mL). The aqueous layer was extracted with EtOAc (2×10 mL). The combined organics were dried over MgSO$_4$, filtered, and concentrated. The residue was purified by column chromatography using an Analogix® Intelliflash280™ (SiO$_2$, eluted with a gradient of 5-30% solvent A in EtOAc, solvent A: 9:1 methanol:triethylamine) to afford the title compound (140 mg, 57% yield). $^1$H NMR (300 MHz, DMSO-d$_6$)

δ ppm 0.40-0.53 (m, 4 H), 1.03 (s, 9 H), 1.13-1.26 (m, J=7.46 Hz, 1 H), 1.38 (s, 9 H), 2.81 (t, J=5.59 Hz, 2 H), 3.91 (s, 3 H), 4.12 (t, J=5.59 Hz, 2 H), 4.17 (d, J=7.12 Hz, 2 H), 6.85 (s, 1 H), 7.18 (d, J=8.48 Hz, 1 H), 7.59 (dd, J=8.48, 2.03 Hz, 1 H), 7.70 (d, J=2.37 Hz, 1 H); MS (ESI) m/z 495 [M+H]$^+$, 493 [M−H].

Example 2

2-[(1-tert-butylazetidin-3-yl)oxy]-N-[(3E)-5-tert-butyl-2-(cyclopropylmethyl)-1-methyl-1,2-dihydro-3H-pyrazol-3-ylidene]-5-(trifluoromethyl)benzamide The title compound (52.5% yield) was prepared and purified according to the procedure described in Example 1H, substituting 1-tert-butylazetidin-3-ol for 2-(tert-butylamino)ethanol. $^1$H NMR (300 MHz, DMSO-d$_6$) δ ppm 0.41-0.53 (m, 4 H), 0.91 (s, 9H), 1.12-1.25 (m, 1 H), 1.39 (s, 9 H), 3.09 (dd, J=7.63, 5.59 Hz, 2 H), 3.54 (dd, J=7.63, 5.93 Hz, 2 H), 3.91 (s, 3 H), 4.16 (t, J=7.12 Hz, 2 H) 4.69-4.79 (m, 1 H), 6.80 (s, 1 H), 6.91 (d, J=8.48 Hz, 1 H), 7.51-7.56 (m, 1 H), 7.68 (d, J=2.03 Hz, 1 H); MS (ESI) m/z 507 [M+H]$^+$, 505 [M−H].

Example 3

Example 3A

N-(5-tert-butyl-1,3,4-thiadiazol-2-yl)-2-fluoro-5-(trifluoromethyl)benzamide

To a solution of 5-tert-butyl-1,3,4-thiadiazol-2-amine (1.57 g, 10 mmol) and 2-fluoro-5-(trifluoromethyl)benzoyl chloride (2.27 g, 10 mmol) in CH$_2$Cl$_2$ (45 mL) at 0° C. was added triethylamine (1.7 mL, 12 mmol) dropwise and the reaction mixture was allowed to warm to ambient temperature for 12 hours. The mixture was then washed with water, brine, dried with MgSO$_4$, filtered, and concentrated under reduced pressure to afford 3.2 g of the title compound. MS (DCI/NH$_3$) m/z 348 (M+H)$^+$.

Example 3B

N-[(2Z)-3-butyl-5-tert-butyl-1,3,4-thiadiazol-2(3H)-ylidene]-2-fluoro-5-(trifluoromethyl)benzamide A mixture of Example 3A (348 mg, 1 mmol), 1-iodobutane (551 mg, 3 mmol) and potassium carbonate (276 mg, 2 mmol) in toluene (25 mL) was treated with tetrabutylammonium iodide (11 mg, 0.03 mmol), tetrabutylammonium hydrogen sulfate (10 mg, 0.03 mmol) and tetraethylammonium iodide (11 mg, 0.04 mmol) and the resulting mixture was refluxed for 14 hours. The mixture was cooled to room temperature, washed with water, brine, dried with MgSO$_4$, filtered, and concentrated under reduced pressure. The residue was purified by column chromatography using an Analogix® Intelliflash280™ (SiO$_2$, eluted with a gradient of 0-30% EtOAc in hexanes) to afford the title compound (360 mg, 89% yield). $^1$H NMR (300 MHz, CDCl$_3$) δ ppm 1.00 (t, J=7.29 Hz, 3 H), 1.35-1.48 (m, 11 H), 1.84-1.98 (m, 2 H), 4.43 (t, J=7.29 Hz, 2 H), 7.18-7.29 (m, 1 H), 7.71 (dd, J=8.14, 4.07 Hz, 1 H), 8.43-8.53 (m, 1 H); MS (DCI) m/z 404 (M+H)$^+$.

Example 3C

2-[(1-tert-butylazetidin-3-yl)oxy]-N-[(2Z)-3-butyl-5-tert-butyl-1,3,4-thiadiazol-2(3H)-ylidene]-5-(trifluoromethyl)benzamide The title compound (62% yield) was prepared and purified according to the procedure described in Example 1H, substituting Example 3B for Example 1G, and substituted 1-tert-butylazetidin-3-ol for 2-(tert-butylamino)ethanol. $^1$H NMR (300 MHz, DMSO-d$_6$) δ ppm 0.87-0.96 (m, 12 H), 1.24-1.36 (m, 2 H), 1.39 (s, 9 H), 1.75-1.88 (m, 2H), 3.13 (dd, J=7.80, 5.43 Hz, 2 H), 3.55-3.62 (m, 2 H), 4.36 (t, J=6.95 Hz, 2 H), 4.85 (d, J=5.43 Hz, 1 H), 7.07 (d, J=8.82 Hz, 1 H), 7.76 (dd, J=8.82, 2.37 Hz, 1 H), 8.12 (d, J=2.03 Hz, 1 H); MS (ESI) m/z 513 [M+H]$^+$, 511 [M−H]$^−$.

Example 4

2-[2-(tert-butylamino)ethoxy]-N-[(3E)-2-butyl-5-tert-butyl-1-methyl-1,2-dihydro-3H-pyrazol-3-ylidene]-5-(trifluoromethyl)benzamide

Example 4A 3-tert-butyl-1-butyl-1H-pyrazol-5-amine

A mixture of butylhydrazine oxalate (10 g, 56.1 mmol) and 4,4-dimethyl-3-oxopentanenitrile (7.0 g, 56.1 mmol) in ethanol (100 mL) was warmed to 85° C. and stirred for 3 hours. The mixture was cooled to ambient temperature, concentrated under reduced pressure and the residue was partitioned between CH$_2$Cl$_2$ (100 mL) and saturated aqueous NaHCO$_3$ (100 mL). The layers were separated and the aqueous phase was extracted with CH$_2$Cl$_2$ (3×15 mL). The combined organic extracts were dried over Na$_2$SO$_4$, filtered, and concentrated under reduced pressure to provide the title compound (10 g, 51.2 mmol, 91% yield). MS (DCI/NH$_3$) m/z 196 (M+H)$^+$.

Example 4B

N-(1-butyl-3-tert-butyl-1H-pyrazol-5-yl)-2-fluoro-5-(trifluoromethyl)benzamide

To a solution of Example 4A (30.3 g, 155 mmol) and Et$_3$N (64.9 mL, 465 mmol) in THF (500 mL) at ambient temperature was added 2-fluoro-5-(trifluoromethyl)benzoyl chloride (23.5 mL, 155 mmol) dropwise over 30 minutes via syringe pump. The mixture was stirred at ambient temperature for 1 hour then diluted with saturated aqueous NaHCO$_3$ (100 mL) and extracted with EtOAc (200 mL). The layers were separated and the aqueous phase was extracted with EtOAc (3×20 mL). The combined organic extracts were dried over anhydrous Na$_2$SO$_4$, filtered, and concentrated under reduced pressure. Purification of the residue by column chromatography (SiO$_2$, 50% hexanes/EtOAc) provided the title compound (50.3 g, 130 mmol, 84% yield). MS (ESI$^+$) m/z 386 (M+H)$^+$.

Example 4C

N-[(3E)-2-butyl-5-tert-butyl-1-methyl-1,2-dihydro-3H-pyrazol-3-ylidene]-2-fluoro-5-(trifluoromethyl)benzamide To a solution of Example 4B (50.2 g, 130 mmol) in toluene (500 mL) was added methyl trifluoromethanesulfonate (21.4 mL, 195 mmol). The mixture was warmed to 100° C. and stirred for 20 hours. The mixture was cooled to ambient temperature then diluted with water (200 mL) and acetone (500 mL). This solution was stirred for 30 minutes then concentrated NH$_4$OH (100 mL) was added. The mixture was stirred for 30 minutes then partially concentrated under reduced pressure. The residue was diluted with EtOAc (300 mL) and brine (100 mL), the layers were separated and the aqueous phase was extracted with EtOAc (3×30 mL). The combined organic extracts were dried over anhydrous Na$_2$SO$_4$, filtered, and concentrated under reduced pressure. The residue was purified by column chromatography (SiO$_2$, 80% hexanes/EtOAc to 100% EtOAc to 10% MeOH in EtOAc) and the fractions collected and concentrated. The material was then dissolved in EtOAc (150 mL) and was washed with 10% NaOH (100 mL). The layers were separated, the aqueous phase was extracted with EtOAc (3×50 mL) and the combined organic extracts were dried over anhydrous Na$_2$SO$_4$, filtered and concentrated under reduced pressure to give (46.3 g, 116 mmol, 89% yield) the title compound. MS (ESI$^+$) m/z 400 (M+H)$^+$.

Example 4D

2-[2-(tert-butylamino)ethoxy]-N-[(3E)-2-butyl-5-tert-butyl-1-methyl-1,2-dihydro-3H-pyrazol-3-ylidene]-5-(trifluoromethyl)benzamide The title compound was prepared and isolated as described in Example 1H, substituting Example 4C for Example 1G in 74.0% yield. $^1$H NMR (300 MHz, DMSO-d$_6$) δ ppm 0.90 (t, J=7.29 Hz, 3 H) 1.05-1.15 (m, 9 H) 1.23-1.34 (m, 2 H) 1.37 (s, 9 H) 1.55-1.68 (m, 2 H) 2.87-2.97 (m, 2 H) 3.87 (s, 3 H) 4.20 (s, 2 H) 4.27 (t, J=7.29 Hz, 2 H) 6.84 (s, 1 H) 7.24 (d, J=8.14 Hz, 1 H) 7.63 (dd, J=8.82, 2.03 Hz, 1 H) 7.85 (s, 1 H); MS (ESI) m/z 497 (M+H)$^+$, 495 (M–H)$^-$.

Example 5

2-[2-(tert-butylamino)ethoxy]-N-[(3E)-5-tert-butyl-2-(cyclobutylmethyl)-1-methyl-1,2-dihydro-3H-pyrazol-3-ylidene]-5-(trifluoromethyl)benzamide

Example 5A di-tert-butyl 1-(cyclobutylmethyl)hydrazine-1,2-dicarboxylate

The title compound was prepared and isolated as described in Example 1A, substituting cyclobutylmethanol for cyclopropylmethanol in 52% yield. $^1$H NMR (300 MHz, CDCl$_3$) δ ppm 1.40-1.51 (m, 18 H) 1.64-1.78 (m, 2 H) 1.80-1.94 (m, 2 H) 1.96-2.09 (m, 2 H) 2.50-2.63 (m, 1 H) 3.47 (d, J=5.76 Hz, 2 H).

Example 5B (cyclobutylmethyl)hydrazine dihydrochloride

The title compound was prepared and isolated as described in Example 1B, substituting Example 5A for Example 1A in 94% yield. $^1$H NMR (300 MHz, DMSO-d$_6$) δ ppm 1.72-1.87 (m, 4 H) 1.97-2.08 (m, 2 H) 2.50-2.59 (m, 1 H) 2.9 (d, J=7.14 Hz, 2 H).

Example 5C 3-tert-butyl-1-(cyclobutylmethyl)-1H-pyrazol-5-amine

The title compound was prepared and isolated as described in Example 1C, substituting Example 5B for Example 1B in 94% yield. The product was basicfied to obtain the free base. MS (DCI/NH$_3$) m/z 208 (M+H)$^+$

Example 5D

N-(3-tert-butyl-1-(cyclobutylmethyl)-1H-pyrazol-5-yl)-2,2,2-trifluoroacetamide

The title compound was prepared and isolated as described in Example 1D, substituting Example 5C for Example 1C in 71% yield. $^1$H NMR (300 MHz, CDCl$_3$) δ ppm 1.28 (s, 9 H) 1.73-1.89 (m, 4 H) 1.98-2.10 (m, 2 H) 2.75 (dt, J=15.07, 7.54 Hz, 1 H) 3.94-4.00 (m, 2 H) 6.27 (s, 1 H); MS (ESI) m/z 304 [M+H]$^+$.

Example 5E (E)-N-(5-tert-butyl-2-(cyclobutylmethyl)-1-methyl-1H-pyrazol-3(2H)-ylidene)-2,2,2-trifluoroacetamide The title compound was prepared and isolated as described in Example 1E, substituting Example 5D for Example 1D in 54% yield. $^1$H NMR (300 MHz, CDCl$_3$) δ ppm 1.41 (s, 9 H) 1.85-1.94 (m, 5 H) 1.98-2.03 (m, 1 H) 2.58-2.63 (m, 1 H) 3.78 (s, 3 H) 4.37 (d, J=7.54 Hz, 2 H) 6.93 (s, 1 H); MS (ESI) m/z 318 [M+H]$^+$.

Example 5F 5-tert-butyl-2-(cyclobutylmethyl)-1-methyl-1H-pyrazol-3(2H)-imine The title compound was prepared and isolated as described in Example 1F, substituting Example 5E for Example 1E in 91% yield. MS (DCI/NH$_3$) m/z 222 (M+H)$^+$.

Example 5G (E)-N-(5-tert-butyl-2-(cyclobutylmethyl)-1-methyl-1H-pyrazol-3(2H)-ylidene)-2-fluoro-5-(trifluoromethyl)benzamide The title compound was prepared and isolated as described in Example 1G, substituting Example 5F for Example 1F in 90% yield. $^1$H NMR (300 MHz, CDCl$_3$) δ ppm 1.43 (s, 9 H) 1.87-1.97 (m, 4 H) 1.99-2.07 (m, 2 H) 2.61-2.73 (m, 1 H) 3.76 (s, 3 H) 4.42-4.46 (m, 2 H) 7.10 (s, 1 H) 7.16 (t, J=9.32 Hz, 1 H) 7.54-7.61 (m, 1 H) 8.37 (d, J=2.03 Hz, 1 H); MS (DCI) m/z 412 [M+H]$^+$.

Example 5H

2-[2-(tert-butylamino)ethoxy]-N-[(3E)-5-tert-butyl-2-(cyclobutylmethyl)-1-methyl-1,2-dihydro-3H-pyrazol-3-ylidene]-5-(trifluoromethyl)benzamide The title compound was prepared and isolated as described in Example 1H, substituting Example 5G for Example 1G in 64% yield. $^1$H NMR (300 MHz, DMSO-d$_6$) δ ppm 1.02 (s, 9 H) 1.36 (s, 9 H) 1.82 (d, J=2.38 Hz, 4 H) 1.90-1.98 (m, 2 H) 2.61-2.74 (m, 1H) 2.78 (t, J=5.55 Hz, 2 H) 3.80 (s, 3 H) 4.11 (t, J=5.55 Hz, 2 H) 4.33 (d, J=7.14 Hz, 2 H) 6.85 (s, 1 H) 7.18 (d, J=8.72 Hz, 1 H) 7.59 (dd, J=8.53, 2.18 Hz, 1 H) 7.77 (d, J=2.38 Hz, 1H); MS (ESI) m/z 509 (M+H)$^+$, 507 (M–H)$^-$.

Example 6

N-[(3E)-5-tert-butyl-2-(cyclobutylmethyl)-1-methyl-1,2-dihydro-3H-pyrazol-3-ylidene]-2-{[(3S)-1-methylpyrrolidin-3-yl]oxy}-5-(trifluoromethyl)benzamide The title compound was prepared according to the procedure described in Example 1H, substituting Example 5G for Example 1G, and (S)-1-methylpyrrolidin-3-ol for 2-(tert-butylamino)ethanol to provide title compound as white solid with 71% yield. $^1$H NMR (300 MHz, DMSO-$d_6$) δ ppm 1.37 (s, 9 H) 1.74-1.86 (m, 4 H) 1.89-1.98 (m, 2 H) 2.25-2.29 (m, 4 H) 2.37-2.51 (m, 2 H) 2.57-2.74 (m, 3 H) 2.83 (dd, J=10.34, 5.93 Hz, 1 H) 3.81 (s, 3H) 4.33 (d, J=7.46 Hz, 2 H) 4.90-5.03 (m, 1 H) 6.80 (s, 1 H) 7.09 (d, J=8.48 Hz, 1 H) 7.56 (dd, J=8.99, 2.20 Hz, 1 H) 7.74 (d, J=2.37 Hz, 1 H); MS (ESI) m/z 466 (M+H)$^+$, 464 (M−H)$^-$.

It is understood that the foregoing detailed description and accompanying examples are merely illustrative and are not to be taken as limitations upon the scope of the invention, which is defined solely by the appended claims and their equivalents. Various changes and modifications to the disclosed embodiments are apparent to those skilled in the art. Such changes and modifications, including without limitation those relating to the chemical structures, substituents, derivatives, intermediates, syntheses, formulations and/or methods of use of the invention, can be made without departing from the spirit and scope thereof.

The invention claimed is:

1. A compound according to formula (I), or a pharmaceutically acceptable salt, solvate, salt of a solvate, prodrug, salt of a prodrug, or a combination thereof

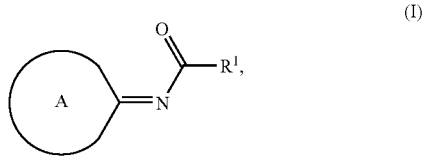

(I)

wherein
- $R^1$ is aryl, heteroaryl, heterocycle, cycloalkyl, or cycloalkenyl; each of which is substituted by one $R^x$ group and each is optionally further substituted with 1, 2, 3, or 4 $R^y$ group(s);
- $R^x$ is —O—$(CR^{1a}R^{1b})_{q1}$—$N(R^{1m})_2$ or —O-$G^1$;
- each $R^y$ is independently $G^{1d}$, alkyl, alkenyl, alkynyl, halogen, haloalkyl, =N—CN, $NO_2$, =N—$OR^f$, —CN, oxo, —$OR^f$, —$OC(O)R^f$, —$OC(O)N(R^f)_2$, —$S(O)_2R^e$, —$S(O)_2N(R^f)_2$, —$C(O)R^f$, —$C(O)OR^f$, —$C(O)N(R^f)_2$, —$N(R^f)_2$, —$N(R^f)C(O)R^f$, —$N(R^f)S(O)_2R^e$, —$N(R^f)C(O)O(R^e)$, —$N(R^f)C(O)N(R^f)_2$, —$N(R^f)S(O)_2N(R^f)_2$, —$(CR^{1c}R^{1d})_{q2}$—$OR^f$, —$(CR^{1c}R^{1d})_{q2}$—$OC(O)R^f$, —$(CR^{1c}R^{1d})_{q2}$—$OC(O)N(R^f)_2$, —$(CR^{1c}R^{1d})_{q2}$—$S(O)_2R^e$, —$(CR^{1c}R^{1d})_{q2}$—$S(O)_2N(R^f)_2$, —$(CR^{1c}R^{1d})_{q2}$—$C(O)R^f$, —$(CR^{1c}R^{1d})_{q2}$—$C(O)OR^f$, —$(CR^{1c}R^{1d})_{q2}$—$C(O)N(R^f)_2$, —$(CR^{1c}R^{1d})_{q2}$—$N(R^f)_2$, —$(CR^{1c}R^{1d})_{q2}$—$N(R^f)C(O)R^f$, —$(CR^{1c}R^{1d})_{q2}$—$N(R^f)S(O)_2R^e$, —$(CR^{1c}R^{1d})_{q2}$—$N(R^f)C(O)O(R^e)$, —$(CR^{1c}R^{1d})_{q2}$—$N(R^f)C(O)N(R^f)_2$, —$(CR^{1c}R^{1d})_{q2}$—$N(R^f)S(O)_2N(R^f)_2$, or —$(CR^{1c}R^{1d})_{q2}$—CN;
- $R^{1m}$, at each occurrence, is independently, hydrogen or $C_1$-$C_4$ alkyl;
- $R^{1a}$, at each occurrence, is independently hydrogen or $C_1$-$C_4$ alkyl;
- $R^{1b}$, at each occurrence, is independently hydrogen or $C_1$-$C_4$ alkyl;
- $G^1$ is cycloalkyl, cycloalkenyl, aryl, heterocycle, or heteroaryl; each of which is optionally substituted with 1, 2, 3, 4, 5, or 6 substituents independently selected from the group consisting of oxo, alkyl, alkenyl, alkynyl, halogen, haloalkyl, =N—CN, —C(=NOR$^f$)R$^a$, =N—OR$^f$, —CN, $NO_2$, oxo, —$OR^a$, —$OC(O)R^a$, —$OC(O)N(R^b)(R^c)$, —$S(O)R^d$, —$S(O)_2R^d$, —$S(O)_2N(R^b)(R^c)$, —$C(O)R^a$, —$C(O)OR^a$, —$C(O)N(R^b)(R^c)$, —$N(R^b)(R^c)$, —$N(R^c)C(O)R^a$, —$N(R^c)S(O)_2R^d$, —$N(R^c)C(O)O(R^a)$, —$N(R^c)S(O)_2N(R^b)(R^c)$, —$N(R^c)C(O)N(R^b)(R^c)$, —$(CR^{1c}R^{1d})_{q3}$—$OR^a$, —$(CR^{1c}R^{1d})_{q3}$—$OC(O)R^a$, —$(CR^{1c}R^{1d})_{q3}$—$OC(O)N(R^b)(R^c)$, —$(CR^{1c}R^{1d})_{q3}$—$S(O)R^d$, —$(CR^{1c}R^{1d})_{q3}$—$S(O)_2R^d$, —$(CR^{1c}R^{1d})_{q3}$—$S(O)_2N(R^b)(R^c)$, —$(CR^{1c}R^{1d})_{q3}$—$C(O)R^a$, —$(CR^{1c}R^{1d})_{q3}$—$C(O)OR^a$, —$(CR^{1c}R^{1d})_{q3}$—$C(O)N(R^b)(R^c)$, —$(CR^{1c}R^{1d})_{q3}$—$N(R^b)(R^c)$, —$(CR^{1c}R^{1d})_{q3}$—$N(R^c)C(O)R^a$, —$(CR^{1c}R^{1d})_{q3}$—$N(R^c)S(O)_2R^d$, —$(CR^{1c}R^{1d})_{q3}$—$N(R^c)C(O)O(R^a)$, —$(CR^{1c}R^{1d})_{q3}$—$N(R^c)S(O)_2N(R^b)(R^c)$, —$(CR^{1c}R^{1d})_{q3}$—$N(R^c)C(O)N(R^b)(R^c)$, and —$(CR^{1c}R^{1d})_{q3}$—CN;
- $R^a$ and $R^c$, at each occurrence, are each independently hydrogen, alkyl, haloalkyl, —$(CR^{1a'}R^{1b'})_{q4}$-$A^3$, $G^{1d}$, or —$(CR^{1a'}R^{1b'})_{q4}$-$G^{1d}$;
- $R^b$, at each occurrence, is independently hydrogen, alkyl, haloalkyl, alkoxyalkyl, monocyclic cycloalkyl, —$(CR^{1c}R^{1d})_{q4}$-(monocyclic cycloalkyl), or haloalkoxyalkyl;
- $R^d$, at each occurrence, is independently alkyl, haloalkyl, —$(CR^{1a'}R^{1b'})_{q4}$-$A^3$, $G^{1d}$, or —$(CR^{1a'}R^{1b'})_{q4}$-$G^{1d}$;
- $G^{1d}$, at each occurrence, is independently a monocyclic heterocycle, a monocyclic heteroaryl, a phenyl, a monocyclic cycloalkyl, or a monocyclic cycloalkenyl; optionally substituted with 1, 2, 3, or 4 substituents independently selected from the group consisting of —$N(R^h)_2$, —CN, oxo, alkyl, haloalkyl, alkoxy, haloalkoxy, halogen, and —OH;
- each occurrence of $A^3$ is independently —$C(O)R^h$, —$S(O)_2R^e$, —$C(O)N(R^h)_2$, —$C(S)N(R^{11})_2$, —$S(O)_2N(R^h)_2$, —$C(=NOR^h)R^h$, —$N(R^h)C(O)R^h$, —$N(R^h)C(O)OR^e$, —$N(R^h)S(O)_2R^e$, —$N(R^h)C(O)N(R^h)_2$, —$N(R^h)S(O)_2N(R^h)_2$, —CN, —$OR^h$, or —$N(R^h)_2$;
- $R^e$, at each occurrence, is independently $C_1$-$C_4$ alkyl, $C_1$-$C_4$ haloalkyl, monocyclic cycloalkyl, monocyclic heterocycle, or —$(CR^{1c}R^{1d})_{q4}$-(monocyclic cycloalkyl);
- $R^f$, at each occurrence, is independently hydrogen, $C_1$-$C_4$ alkyl, $C_1$-$C_4$ haloalkyl, —$(CR^{1c}R^{1d})_{q4}$—$OR^h$, monocyclic heterocycle, monocyclic cycloalkyl, or —$(CR^{1c}R^{1d})_{q4}$-(monocyclic cycloalkyl);
- $R^h$, at each occurrence, is independently hydrogen, $C_1$-$C_4$ alkyl, $C_1$-$C_4$ haloalkyl, monocyclic heterocycle, monocyclic cycloalkyl, or —$(CR^{1c}R^{1d})_{q4}$-(monocyclic cycloalkyl);
- Ring A represents formula (a), (b), (c), or (d)

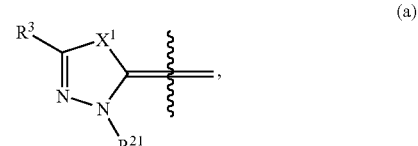

(a)

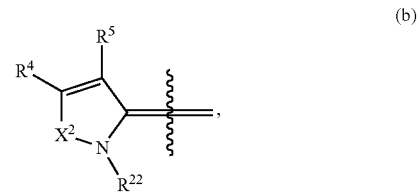

(b)

-continued

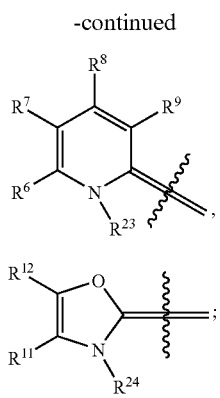

(c)

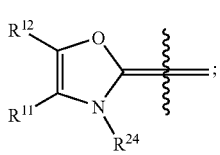

(d)

$R^{21}$, $R^{22}$, $R^{23}$, and $R^{24}$ are each independently alkyl, alkenyl, alkynyl, haloalkyl, $-(CR^{2a}R^{2b})_{q5}-OH$, $-(CR^{2a}R^{2b})_{q5}-O$-alkyl, $-(CR^{2a}R^{2b})_{q5}-O$-haloalkyl, $-(CR^{2a}R^{2b})_{q5}-O-G^2a$, $-(CR^{2a}R^{2b})_{q5}-O-(CR^{2c}R^{2d})_{q6}-G^{2a}$, $-(CR^{2a}R^{2b})_{q6}-C(O)-R^a$, $-(CR^{2a}R^{2b})_{q6}-C(O)O(R^a)$, $-(CR^{2a}R^{2b})_{q6}-C(=N-OR^f)R^a$, $-(CR^{2a}R^{2b})_{q6}-SO_2-R^d$, $-(CR^{2a}R^{2b})_{q6}-G^{2b}$, $-(CR^{2a}R^{2b})_{q6}-C(O)N(R^b)(R^c)$, or $-(CR^{2a}R^{2b})_{q6}-CN$;

each occurrence of $G^{2a}$ is independently cycloalkyl, heterocycle, aryl, or heteroaryl;

$G^{2b}$ is monocyclic cycloalkyl, monocyclic cycloalkenyl, thienyl, or phenyl; each of which is optionally fused with benzo, monocyclic cycloalkyl, monocyclic cycloalkenyl, monocyclic heterocycle, or monocyclic heteroaryl;

$G^{2a}$ and $G^{2b}$, at each occurrence, are each independently unsubstituted or substituted with 1, 2, 3, 4, 5, or 6 substituents independently selected from the group consisting of oxo, alkyl, halogen, $-OH$, alkoxy, haloalkoxy, and haloalkyl;

$R^3$, $R^4$, $R^5$, $R^6$, $R^7$, $R^8$, $R^9$, $R^{11}$, and $R^{12}$ are each independently $G^3$, hydrogen, alkyl, alkenyl, alkynyl, $-NO_2$, $-CN$, halogen, $-OR^h$, $-N(R^h)_2$, $-C(O)R^h$, $-C(O)O(R^h)$, haloalkyl, $-(CR^{3a}R^{3b})_{q7}-OR^h$, $-(CR^{3a}R^{3b})_{q7}-N(R^h)_2$, $-(CR^{3a}R^{3b})_{q7}-C(O)R^h$, or $-(CR^{3a}R^{3b})_{q7}-C(O)O(R^h)$;

$G^3$, at each occurrence, is independently cycloalkyl, cycloalkenyl, aryl, heterocycle or heteroaryl, each of which is independently unsubstituted or substituted with 1, 2, 3, or 4 substituents selected from the group consisting of $C_1$-$C_4$ alkyl, $C_2$-$C_4$ alkenyl, $C_2$-$C_4$ alkynyl, halogen, $C_1$-$C_4$ haloalkyl, $=N-CN$, $=N-OR^h$, oxo, $-OR^h$, $-OC(O)R^h$, $-OC(O)N(R^h)_2$, $-S(O)_2R^e$, $-S(O)_2N(R^h)_2$, $-C(O)R^h$, $-C(O)OR^h$, $-C(O)N(R^h)_2$, $-N(R^h)_2$, $-N(R^h)C(O)R^h$, $-N(R^h)S(O)_2R^e$, $-N(R^h)C(O)O(R^e)$, and $-N(R^h)C(O)N(R^h)_2$;

$R^{1a'}$, at each occurrence, is independently hydrogen, halogen, $C_1$-$C_4$ alkyl, or $C_1$-$C_4$ haloalkyl;

$R^{1b'}$, at each occurrence, is independently hydrogen, halogen, $C_1$-$C_4$ alkyl, $C_1$-$C_4$ haloalkyl, $-OR^h$, $-N(R^h)_2$, $-N(R^h)C(O)R^h$, $-N(R^h)C(O)OR^e$, or $-N(R^h)S(O)_2R^e$;

$R^{1c}$, $R^{1d}$, $R^{2a}$, $R^{2b}$, $R^{2c}$, $R^{2d}$, $R^{3a}$, and $R^{3b}$, at each occurrence, are each independently hydrogen, halogen, $C_1$-$C_4$ alkyl, or $C_1$-$C_4$ haloalkyl;

$X^1$ and $X^2$ are each independently O, S, or $N(R^{10})$ wherein $R^{10}$ is alkyl, alkoxyalkyl, haloalkoxyalkyl, or haloalkyl;

q1 and q5, at each occurrence, are each independently 2, 3, or 4;

q2, q3, q4, q6, and q7, at each occurrence, are each independently 1, 2, 3, 4, 5, or 6; and the monocyclic cycloalkyl and the monocyclic heterocycle, as a substituent or as part of a substituent, of $R^b$, $R^e$, $R^f$, and $R^h$, are each independently unsubstituted or substituted with 1, 2, 3, or 4 substituents independently selected from the group consisting of oxo, $C_1$-$C_4$ alkyl, halogen, $-OH$, $C_1$-$C_4$ alkoxy, $C_1$-$C_4$ haloalkoxy, and $C_1$-$C_4$ haloalkyl;

with the proviso that when $G^1$ is aryl, then $R^{21}$, $R^{22}$, $R^{23}$, and $R^{24}$ are each independently $-(CR^{2a}R^{2b})_{q5}-O-G^{2a}$, $-(CR^{2a}R^{2b})_{q5}-O-(CR^{2c}R^{2d})_{q6}-G^{2a}$, $-(CR^{2a}R^{2b})_{q6}-C(O)-R^a$, $-(CR^{2a}R^{2b})_{q6}-C(=N-OR^f)R^a$, or $-(CR^{2a}R^{2b})_{q6}-SO_2-R^d$.

2. The compound according to claim 1 or a pharmaceutically acceptable salt, solvate, salt of a solvate, prodrug, salt of a prodrug, or a combination thereof wherein $R^1$ is heteroaryl.

3. The compound according to claim 1 having formula (I-i) or a pharmaceutically acceptable salt, solvate, salt of a solvate, prodrug, salt of a prodrug, or a combination thereof

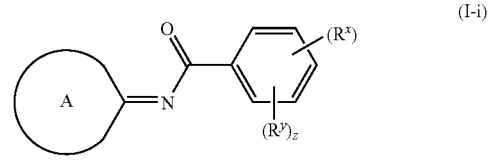

(I-i)

wherein z is 0, 1, 2, 3, or 4, Ring A, $R^x$, and $R^y$ are as set forth in claim 1.

4. The compound according to claim 3 or a pharmaceutically acceptable salt, solvate, salt of a solvate, prodrug, salt of a prodrug, or a combination thereof, wherein $R^x$ is $-O-(CR^{1a}R^{1b})_{q1}-N(R^{1m})_2$.

5. The compound according to claim 3 or a pharmaceutically acceptable salt, solvate, salt of a solvate, prodrug, salt of a prodrug, or a combination thereof, wherein
$R^x$ is $-O-(CR^{1a}R^{1b})_{q1}-N(R^{1m})_2$, and
Ring A is formula (a).

6. The compound according to claim 3 or a pharmaceutically acceptable salt, solvate, salt of a solvate, prodrug, salt of a prodrug, or a combination thereof, wherein
$R^x$ is $-O-(CR^{1a}R^{1b})_{q1}-N(R^{1m})_2$, and
Ring A is formula (b).

7. The compound according to claim 3 or a pharmaceutically acceptable salt, solvate, salt of a solvate, prodrug, salt of a prodrug, or a combination thereof, wherein
$R^x$ is $-O-(CR^{1a}R^{1b})_{q1}-N(R^{1m})_2$,
Ring A is formula (b), and
$X^2$ is $N(R^{10})$.

8. The compound according to claim 3 or a pharmaceutically acceptable salt, solvate, salt of a solvate, prodrug, salt of a prodrug, or a combination thereof, wherein
$R^x$ is $-O-(CR^{1a}R^{1b})_{q1}-N(R^{1m})_2$,
Ring A is formula (b),
$X^2$ is $N(R^{10})$, and
$R^{22}$ is alkyl, haloalkyl, $-(CR^{2a}R^{2b})_{q4}-OH$, $-(CR^{2a}R^{2b})_{q4}-O$-alkyl, $-(CR^{2a}R^{2b})_{q4}-O$-haloalkyl, or $-(CR^{2a}R^{2b})_{q5}-G^{2b}$.

9. The compound according to claim 3 or a pharmaceutically acceptable salt, solvate, salt of a solvate, prodrug, salt of a prodrug, or a combination thereof, wherein $R^x$ is $-O-G^1$.

10. The compound according to claim 3 or a pharmaceutically acceptable salt, solvate, salt of a solvate, prodrug, salt of a prodrug, or a combination thereof, wherein 11. The compound according to claim 3 or a pharmaceutically acceptable salt, solvate, salt of a solvate, prodrug, salt of a prodrug, or a combination thereof, wherein
$R^x$ is —O-$G^1$, and
Ring A is formula (b).

12. The compound according to claim 3 or a pharmaceutically acceptable salt, solvate, salt of a solvate, prodrug, salt of a prodrug, or a combination thereof, wherein
$R^x$ is —O-$G^1$,
Ring A is formula (b), and
$X^2$ is N($R^{10}$).

13. The compound according to claim 3 or a pharmaceutically acceptable salt, solvate, salt of a solvate, prodrug, salt of a prodrug, or a combination thereof, wherein
$R^x$ is —O-$G^1$,
Ring A is formula (b),
$X^2$ is N($R^{10}$), and
$R^{22}$ is alkyl, haloalkyl, —$(CR^{2a}R^{2b})_{q4}$—OH, —$(CR^{2a}R^{2b})_{q4}$—O-alkyl, —$(CR^{2a}R^{2b})_{q4}$—O-haloalkyl, or —$(CR^{2a}R^{2b})_{q5}$-$G^{2b}$.

14. The compound according to claim 1 or a pharmaceutically acceptable salt, solvate, salt of a solvate, prodrug, salt of a prodrug, or a combination thereof, wherein Ring A is formula (c), $R^6$ and $R^9$ are hydrogen, $R^7$ and $R^8$ are each independently hydrogen or $C_1$-$C_4$ alkyl, and $R^{23}$ is alkyl, haloalkyl, —$(CR^{2a}R^{2b})_{q4}$—OH, —$(CR^{2a}R^{2b})_{q4}$—O-alkyl, —$(CR^{2a}R^{2b})_{q4}$—O-haloalkyl, or —$(CR^{2a}R^{2b})_{q5}$-$G^{2b}$.

15. The compound according to claim 1 or a pharmaceutically acceptable salt, solvate, salt of a solvate, prodrug, salt of a prodrug, or a combination thereof, wherein Ring A is formula (d), $R^{11}$ and $R^{12}$ are each independently hydrogen, halogen, or alkyl, and $R^{24}$ is alkyl, haloalkyl, —$(CR^{2a}R^{2b})_{q4}$—OH, —$(CR^{2a}R^{2b})_{q4}$—O-alkyl, —$(CR^{2a}R^{2b})_{q4}$—O-haloalkyl, or —$(CR^{2a}R^{2b})_{q5}$-$G^{2b}$.

16. The compound according to claim 1 or a pharmaceutically acceptable salt, solvate, salt of a solvate, prodrug, salt of a prodrug, or a combination thereof, selected from the group consisting of 2-[2-(tert-butylamino)ethoxy]-N-[(3E)-5-tert-butyl-2-(cyclopropylmethyl)-1-methyl-1,2-dihydro-3H-pyrazol-3-ylidene]-5-(trifluoromethyl)benzamide;
2-[(1-tert-butylazetidin-3-yl)oxy]-N-[(3E)-5-tert-butyl-2-(cyclopropylmethyl)-1-methyl-1,2-dihydro-3H-pyrazol-3-ylidene]-5-(trifluoromethyl)benzamide;
2-[(1-tert-butylazetidin-3-yl)oxy]-N-[(2Z)-3-butyl-5-tert-butyl-1,3,4-thiadiazol-2(3H)-ylidene]-5-(trifluoromethyl)benzamide;
2-[2-(tert-butylamino)ethoxy]-N-[(3E)-2-butyl-5-tert-butyl-1-methyl-1,2-dihydro-3H-pyrazol-3-ylidene]-5-(trifluoromethyl)benzamide;
2-[2-(tert-butylamino)ethoxy]-N-[(3E)-5-tert-butyl-2-(cyclobutylmethyl)-1-methyl-1,2-dihydro-3H-pyrazol-3-ylidene]-5-(trifluoromethyl)benzamide; and
N-[(3E)-5-tert-butyl-2-(cyclobutylmethyl)-1-methyl-1,2-dihydro-3H-pyrazol-3-ylidene]-2-{[(3S)-1-methylpyrrolidin-3-yl]oxy}-5-(trifluoromethyl)benzamide.

17. A pharmaceutical composition comprising a therapeutically effective amount of a compound of formula (I) according to claim 1 or a pharmaceutically acceptable salt, solvate, or salt of a solvate thereof, in combination with a pharmaceutically acceptable carrier.

18. A method for treating pain in a mammal in need of such treatment comprising administering to the mammal a therapeutically effective amount of a compound of formula (I) according to claim 1, or a pharmaceutically acceptable salt, solvate, or salt of a solvate thereof.

19. A method of treating, neuropathic pain, nociceptive pain, inflammatory pain, cancer pain, or osteoarthritis pain in a mammal in need thereof, said method comprises administering to the mammal a therapeutically effective amount of a compound of formula (I) according to claim 1, or a pharmaceutically acceptable salt, solvate, or salt of a solvate thereof.

20. A method for providing neuroprotection in a mammal in need of such treatment comprising administering to the mammal a therapeutically effective amount of a compound of formula (I) according to claim 1, or a pharmaceutically acceptable salt, solvate, or salt of a solvate thereof.

* * * * *